US012606791B2

(12) United States Patent (10) Patent No.: US 12,606,791 B2
Mi et al. (45) Date of Patent: Apr. 21, 2026

(54) GRAVITATIONAL LIQUID-SPLITTING DEVICE, CELL PASSAGING DEVICE WITH THE SAME, AND CELL PASSAGING METHOD

(71) Applicant: DRSIGNAL BIOTECHNOLOGY CO., LTD., Taipei City (TW)

(72) Inventors: Hsin-Wu Mi, Taipei City (TW);
Chih-Huang Lin, Taipei City (TW);
Hsin-Fei Huang, Taipei City (TW);
Chia-I Hsu, Taipei City (TW)

(73) Assignee: DRSignal BioTechnology Co., Ltd.,
Taipei City (TW)

( * ) Notice: Subject to any disclaimer, the term of this
patent is extended or adjusted under 35
U.S.C. 154(b) by 658 days.

(21) Appl. No.: 18/156,732

(22) Filed: Jan. 19, 2023

(65) Prior Publication Data

US 2024/0247225 A1 Jul. 25, 2024

(51) Int. Cl.
*C12M 1/00* (2006.01)
*C12M 1/26* (2006.01)
(Continued)

(52) U.S. Cl.
CPC ............ *C12M 47/02* (2013.01); *C12M 23/40*
(2013.01); *C12M 33/10* (2013.01); *C12M
41/36* (2013.01);
(Continued)

(58) Field of Classification Search
CPC ...... C12M 47/02; C12M 23/40; C12M 33/10;
C12M 41/36; C12M 41/48; C12M 47/04;
(Continued)

(56) References Cited

U.S. PATENT DOCUMENTS 10,465,156 B2 * 11/2019 Jaeger .................... C12M 41/00
2006/0257999 A1 11/2006 Chang
(Continued)

FOREIGN PATENT DOCUMENTS

CN 108531360 A 9/2018
CN 211837967 U * 11/2020
(Continued)

OTHER PUBLICATIONS

Eggert, Armin, et al. "Liquid-liquid centrifugal separation—New
equipment for optical (photographic) evaluation at laboratory scale."
Chemical Engineering Research and Design 127 (2017): 170-179.

*Primary Examiner* — Benjamin R Whatley
(74) *Attorney, Agent, or Firm* — Rosenberg, Klein & Lee

(57) ABSTRACT

A gravitational liquid-splitting device has a funnel, a dispensing valve, a liquid-splitting part, and a stirring assembly. The funnel has an inner space and a bottom opening connected to each other. The dispensing valve is mounted to the funnel and is configured to close or open the bottom opening of the funnel. The liquid-splitting part is connected to a bottom of the funnel and has an input channel and two output channels. The input channel is formed in the liquid-splitting part and extends upward and downward. An upper end of the input channel forms an input opening on a top of the liquid-splitting part and is connected to the bottom opening of the funnel. The stirring assembly has a stirrer configured to stir liquid in the funnel. Therefore, the gravitational liquid-splitting device improves efficiency and quality, and also reduces risk of contamination in the cell passaging operation.

12 Claims, 28 Drawing Sheets

(51) Int. Cl.

| | |
|---|---|
| *C12M 1/34* | (2006.01) |
| *C12M 1/36* | (2006.01) |
| *G01N 15/1434* | (2024.01) |
| *G01N 35/02* | (2006.01) |
| *G01N 35/10* | (2006.01) |
| *G01N 15/14* | (2006.01) |
| *G01N 35/00* | (2006.01) |

(52) U.S. Cl.

CPC ............ *C12M 41/48* (2013.01); *C12M 47/04* (2013.01); *G01N 15/1434* (2013.01); *G01N 35/025* (2013.01); *G01N 35/10* (2013.01); *G01N 2015/1486* (2013.01); *G01N 2035/00495* (2013.01); *G01N 2035/00534* (2013.01)

(58) Field of Classification Search

CPC .. G01N 15/1434; G01N 35/025; G01N 35/10; G01N 2015/1486; G01N 2035/00495; G01N 2035/00534

See application file for complete search history.

(56) References Cited

U.S. PATENT DOCUMENTS

| | | |
|---|---|---|
| 2016/0326489 A1 | 11/2016 | Durack |
| 2017/0226465 A1 | 8/2017 | Kimura |
| 2020/0025782 A1 | 1/2020 | Ahlfors |

FOREIGN PATENT DOCUMENTS

| | | |
|---|---|---|
| CN | 113046223 A | 6/2021 |
| JP | 2022-125742 A | 8/2022 |
| WO | 2015/005299 A1 | 1/2015 |
| WO | 2015141612 A1 | 9/2015 |
| WO | 2020247832 A1 | 12/2020 |

* cited by examiner

GRAVITATIONAL LIQUID-SPLITTING DEVICE, CELL PASSAGING DEVICE WITH THE SAME, AND CELL PASSAGING METHOD

BACKGROUND OF THE INVENTION

1. Field of the Invention

The present invention relates to a cell passaging device, especially to a device that is configured to split liquid or liquid with cells equally between different containers using gravity.

2. Description of the Prior Arts

Cell passaging is done when the cultured cells, such as human stem cells, are 90%-100% confluent. First, an enzyme and related solution(s) are added to the culture vessel to make the cultured cells detach from a surface of the culture vessel, and then the solution with detached cells (hereinafter referred to as "cell solution") are equally dispensed into double centrifuge tubes, and finally the detached cells are separated from the solutions by using a centrifuge. The cells separated by the centrifuge are transferred to different kinds of containers for subsequent cell passaging process or other processes such as cryo-preservation or bottling for shipping.

When manually dispensing the cell solution to the centrifuge tubes, the cell solution must be split equally for the double centrifuge tubes either volume-wise or weight-wise to balance the centrifuge. The existing manual procedure for splitting the cell solution for the double centrifuge tubes is too complicated and time consuming, and therefor is unsuitable and troublesome for directly converting to an automated process.

Peristaltic pumps are generally used to dispense the liquid or cell solution into the containers, such as centrifuge tubes. Though the peristaltic pumps are capable of precisely controlling a flow of the liquid or the cell solution, a part of the cell solution is stranded in the pump due to significant length of the tubing in the pump, and therefore some of the cells are lost each time when the cell solution is dispensed by the pump.

However, a total amount of the cell solution to be transferred for the cell subculture is limited, and each milliliter of the cell solution comprises a significant amount of cells; therefore, using the peristaltic pump to dispense the cell solution results in loss of a great deal of precious cells.

Moreover, in order to dispense the cell solution, the peristaltic pump inevitably has to pressurize the cell solution, and the pressure difference in the peristaltic pump causes damage to the cells. As a result, the use of the peristaltic pump reduces efficiency of the cell passaging and increases cost of cell passaging.

Additionally, several steps need to be performed before transferring the cell solution to different containers in the cell passaging process. For adherent cells, an enzyme and related solution(s) has to be added to make the cells detach from the surface of the culture vessel. However, currently all steps are performed manually, and are therefore time-consuming, difficult to control quality; risk of contamination due to improper handling is also needed to take into consideration.

To overcome the shortcomings, the present invention provides a gravitational liquid-splitting device, a cell passaging device with the same, and a cell passaging method to mitigate or obviate the aforementioned problems.

SUMMARY OF THE INVENTION

In view of the problems of the conventional cell passaging, when using automated equipment to transfer a solution with detached cells, the solutions with detached cells from multiple cell culture containers are first collected in a specialized container, and then a gravitational liquid-splitting device is used to split the collected solution with detached cells equally between two centrifuge containers, and then the two centrifuge containers are disposed symmetrically in a centrifuge for centrifugation, thereby ensuring dynamic balance during centrifugation.

The main objective of the present invention is to provide a gravitational liquid-splitting device, a cell passaging device with the same, and a cell passaging method to mitigate loss of cells when the solution with detached cells is being transferred to different containers.

The gravitational liquid-splitting device has a funnel, a dispensing valve, a liquid-splitting part, and a stirring assembly. The funnel has an inner space and a bottom opening connected to the bottom of the funnel. The dispensing valve is mounted to the funnel and is configured to close or open the bottom opening of the funnel. The liquid-splitting part is connected to a bottom of the funnel and has an input channel and two output channels. The input channel is formed in the liquid-splitting part and extends upward and downward. An upper end of the input channel forms an input opening on a top of the liquid-splitting part and is connected to the bottom opening of the funnel. The two output channels are formed in the liquid-splitting part. Each of the output channels has a first end and a second end. The first end is connected to a lower end of the input channel. The second end extends inclinedly downward and is connected to an exterior of the liquid-splitting part. The stirring assembly has a funnel and a stirrer. The funnel cover detachably covers an upper opening of the funnel. The stirrer is connected to the funnel cover and is configured to stir liquid in the funnel.

The cell passaging device is configured to dispense contents collected from multiple cell culture containers into two centrifuge containers by gravity. The cell passaging device has a base, a container-handling device, and a liquid equal-splitting device. The container-handling device is mounted on the base and has a container-positioning table, multiple container holders, and multiple container-driving assemblies. The container-positioning table is rotatably or movably mounted on the base. The container holders are pivotally mounted on the container-positioning table. Each of the container holders is configured to accommodate one of the cell culture containers or one of the centrifuge containers, and is pivotable to an emptying angle to empty contents in the cell culture container or the centrifuge container. Each of the container-driving assemblies controls an angle of a respective one of the container holders and is configured to rotate the respective one of the container holders to the emptying angle or to sway the respective one of the container holders. The container-positioning table is configured to move each of the container holders to a first injection position. The liquid equal-splitting device is disposed on a side of the container-handling device. The liquid equal-splitting device has a funnel-positioning table and at least one said gravitational liquid-splitting device as mentioned above. The funnel-positioning table is rotatably or movably mounted on the base. The at least one gravitational liquid-splitting device is mounted on the funnel-positioning table.

The funnel-positioning table is configured to move the at least one gravitational liquid-splitting device from a position under the first injection position to a position above the two centrifuge containers such that liquid in the funnel of the at least one gravitational liquid-splitting device flows into the two centrifuge containers via the two output channels respectively.

The cell passaging method comprises: using the gravitational liquid-splitting device to split contents collected from the multiple cell culture containers equally between the two centrifuge containers, and then dispose the two centrifuge containers oppositely in a centrifuge and use the centrifuge to perform centrifugation to separate the cells from the solution.

When using the cell passaging device, first add a solution, which can detach cells from the surface of the cell culture container, into the cell culture container. Then, sway the cell culture container using the container-handling device to uniformly distribute the solution in the cell culture container and make the cells detach from the surface of the cell culture container. Then, rotate the culture container to an emptying angle using the container-handling device to make the cell solution in the cell culture container flow into the gravitational liquid-splitting device located under the cell culture container. Subsequently, the cell solution automatically flows downward and is split into two equal portions by the liquid-splitting part due to gravity, and the two equal portions enter the two centrifuge containers respectively.

The advantages of the present invention are as follows:

First, liquid in the funnel automatically flows downward into the centrifuge containers due to gravity because the liquid-splitting part is disposed under the funnel, the input channel extends upward and downward, and the output channels extend inclinedly downward. Therefore, the present invention prevents loss of cells during transferring operation, avoids damage to the cells under pressurization by using pump, and effectively automates the process of collecting solution with detached cells that are already separated from the cell culture containers together and then split the collected solution with detached cells equally between the two centrifuge containers. As a result, the present invention improves efficiency of cell passaging, increases cell survival rate of cell passaging, and reduces cost of cell passaging.

Second, because the stirrer can continuously stir the solution with detached cells in the funnel, the present invention prevents cells in the solution from clustering together or adhering to surfaces of the channels, thereby keeping flow rates in the two output channels remain equal and ensuring the solution with detached cells is split equally between the two centrifuge containers.

Third, the cell passaging device replaces traditional manual operation by automatically swaying the cell culture container to efficiently detach the adherent cells from the surface of the container, transferring the solution with detached cells into the gravitational liquid-splitting device, and splitting the solution with detached cells equally between the two centrifuge containers, thereby reducing labor-intensity in the cell passaging operation. As a result, the present invention has advantages such as high efficiency, stable quality, and reducing risk of contamination of cell passaging processes.

Other objectives, advantages and novel features of the invention will become more apparent from the following detailed description when taken in conjunction with the accompanying drawings.

DETAILED DESCRIPTION OF THE PREFERRED EMBODIMENTS

Figure 1:
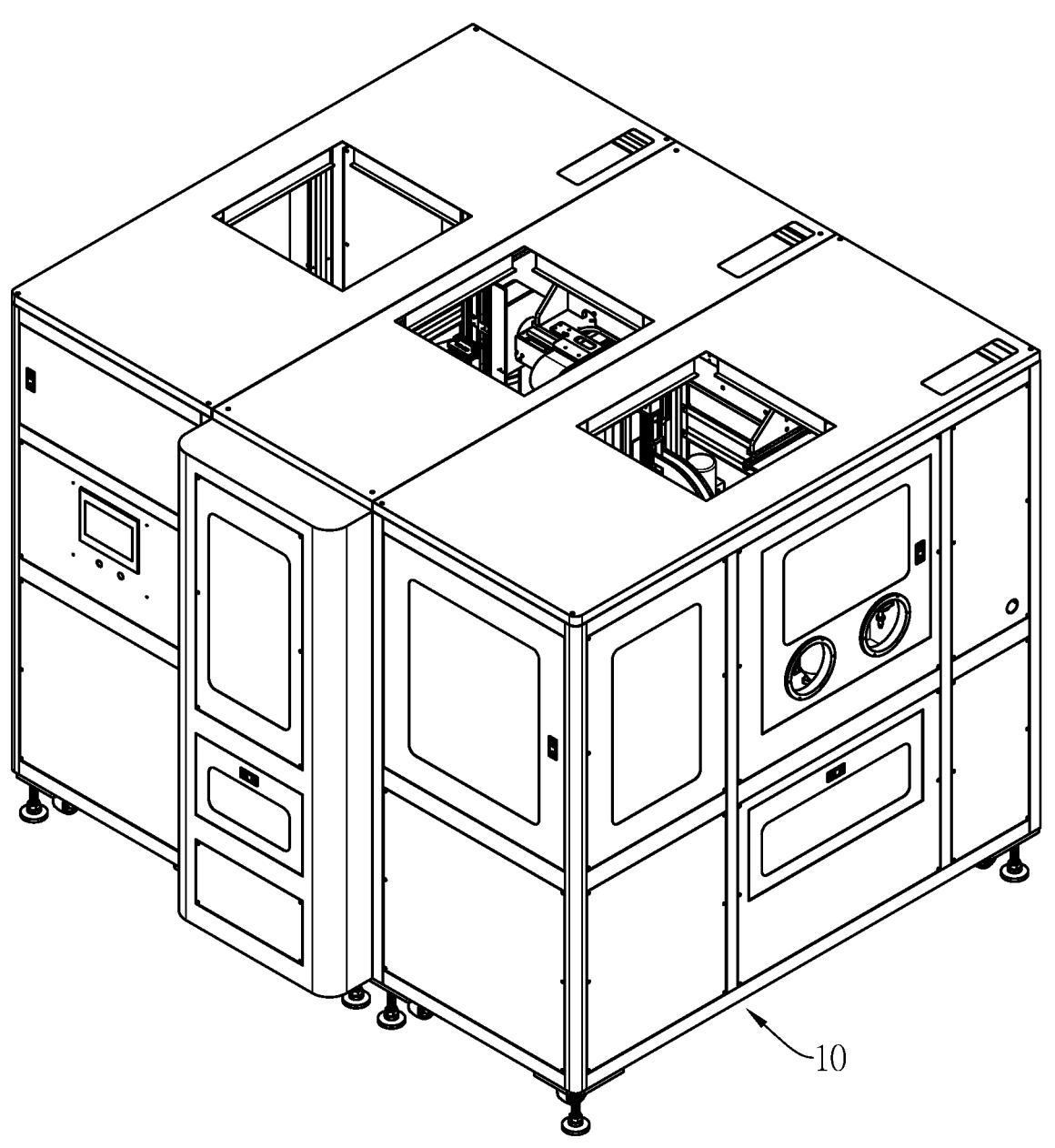
FIG. 1 is a perspective view of a cell passaging device in accordance with the present invention.

With reference to FIGS. 1 to 4 and 28, the cell passaging device in accordance with the present invention is configured to collect contents (i.e. solution with detached cells) from multiple cell culture containers 91, and then split the collected contents between the two centrifuge containers 92 for centrifugation. Cells in solution separated by centrifuge can be used for cell subculture with other cell culture devices. The cell passaging is preferably also configured to transfer the separated cells from solution to cryovials (not shown in figures) for cryopreservation, or to cell solution containers (not shown in figures) for shipments.

The cell culture containers 91 and the centrifuge containers 92 are containers in the same shape preferably. In the preferred embodiment, the culture containers 91 are configured to be put in a centrifuge directly for centrifugation, and therefore the centrifuge containers 92 can be two of the cell culture containers 91 as well.

The cell passaging device has a base 10, a container-handling device 20, and a liquid equal-splitting device 40. In the preferred embodiment, the cell passaging device further has a liquid solution injection device 30, a primary container-moving device 50, an auxiliary container-moving device 60, a centrifuge 70, and an optical inspection device 80.

With reference to FIGS. 4 to 7, the container-handling device 20 is mounted on the base 10 and has a container-positioning table 21, multiple container holders 22, and multiple container-driving assemblies 23.

The container-positioning table 21 is rotatably mounted on the base 10, and is preferably a conventional rotary indexing table. The container-positioning table 21 rotates 90 degrees each time, thereby defining four stationary positions that are fixed in space. The four stationary positions are respectively a container-receiving position 211, a container output position 212, a first injection position 213, and a second injection position 214, wherein the second injection position 214 and the container output position 212 are oppositely disposed on the container-handling device 20.

In the terminology of this technical field, the container-positioning table 21 has four indexed positions: the aforementioned container-receiving position 211, the container output position 212, the first injection position 213, and the second injection position 214 are the four indexed positions of the container-positioning table 21.

A number of the container holders 22 is preferably four; the four container holders 22 are disposed around the container-positioning table 21 at angular intervals of 90 degrees. The container-positioning table 21 is configured to move each container holder 22 cyclically among the container-receiving position 211, the container output position 212, the first injection position 213, and the second injection position 214.

The container-positioning table 21 is not limited to rotary motion. In another preferred embodiment (not shown in figures), the container-positioning table 21 moves the container holder 22 along a straight line or a bent line to move the container holder 22 among multiple specific positions. Moreover, the container-positioning table 21 is not limited to move each container holder 22 to four different positions;

in a less-automated embodiment of the cell passaging device, that is, the container-positioning table 21 only moves the container holder 22 to the first injection position 213.

Figure 7:
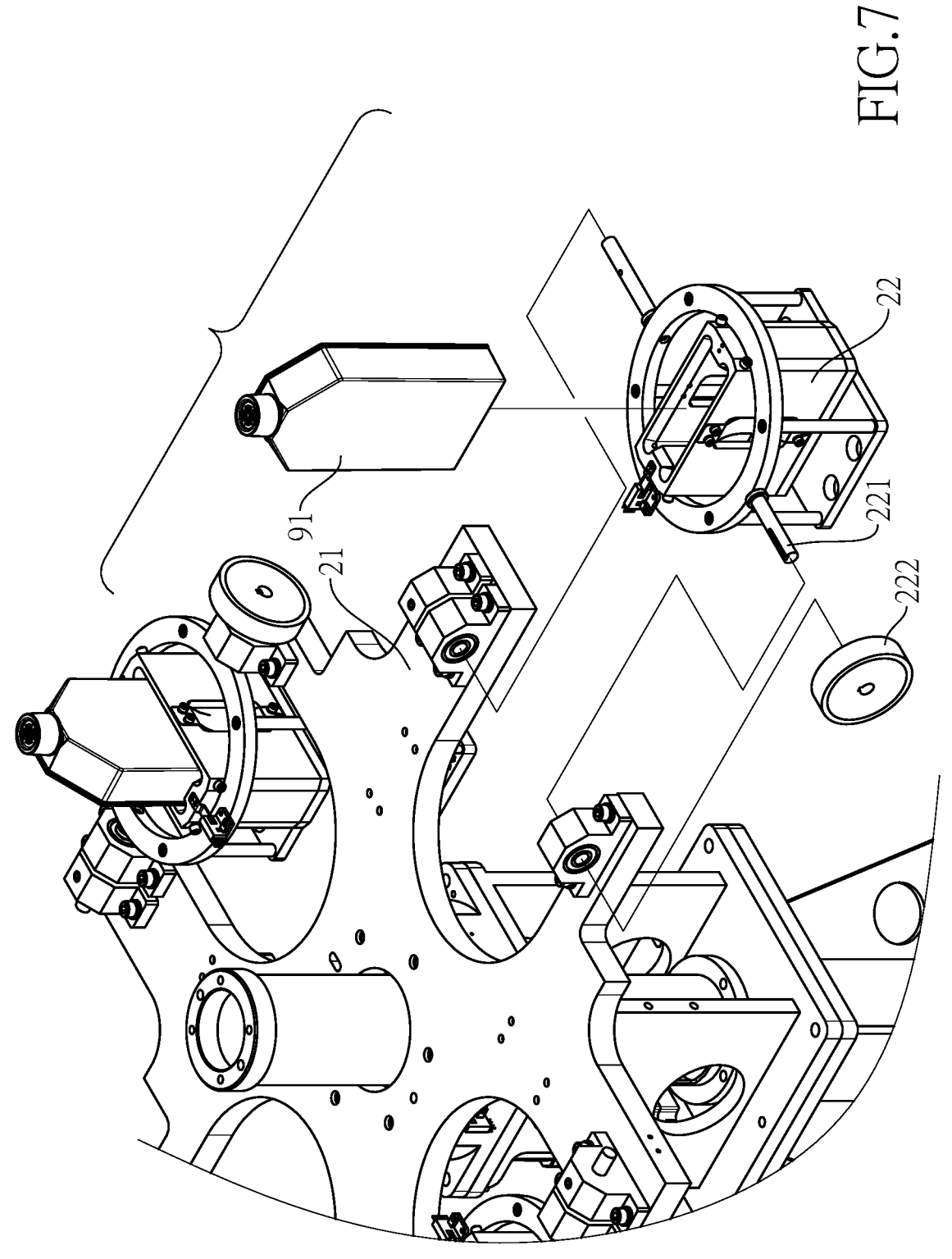
FIG. 7 is an enlarged exploded perspective view of the container-handling device of the cell passaging device in FIG. 6.
Figure 21:
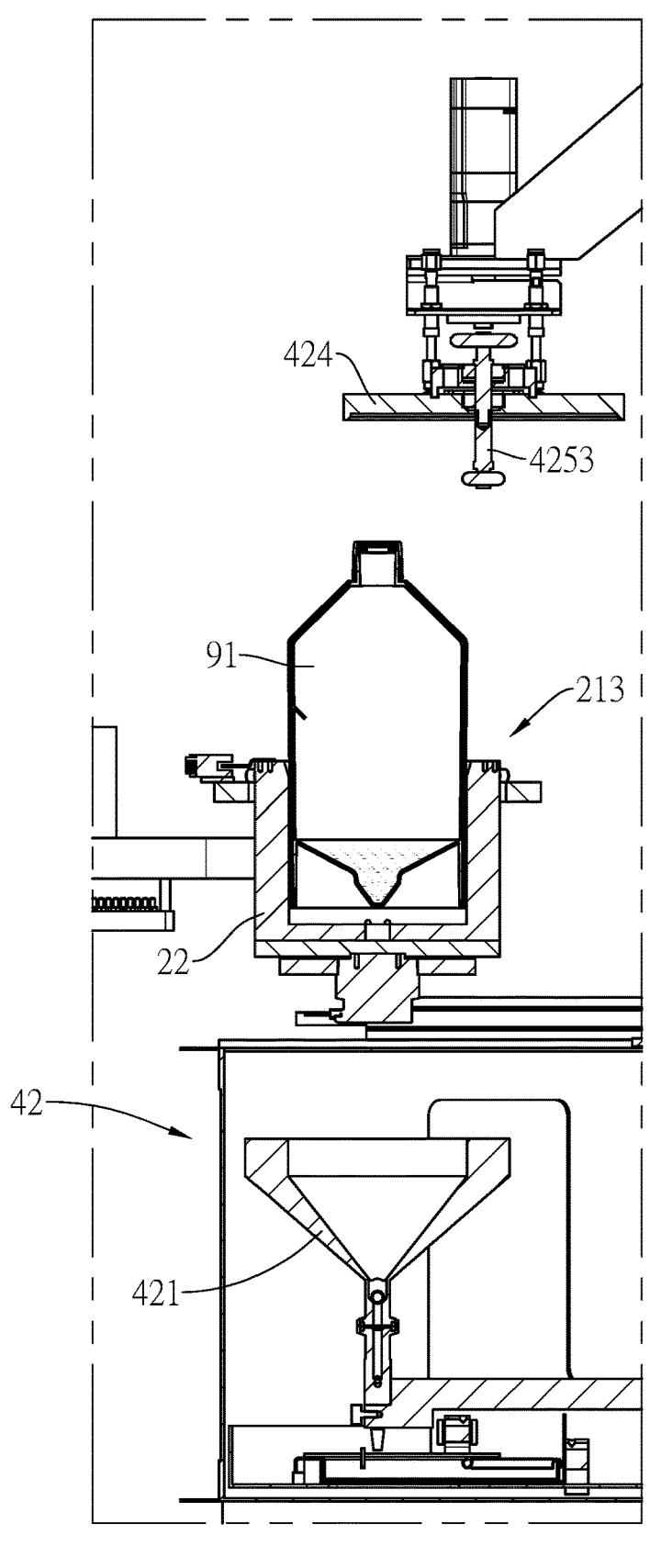
FIGS. 21 and 22 are enlarged sectional views of the container-handling device of the cell passaging device in FIG. 1, showing the cell culture container being rotated to an emptying angle to transfer contents of the cell culture container to the gravitational liquid-splitting device thereunder.
Figure 22:
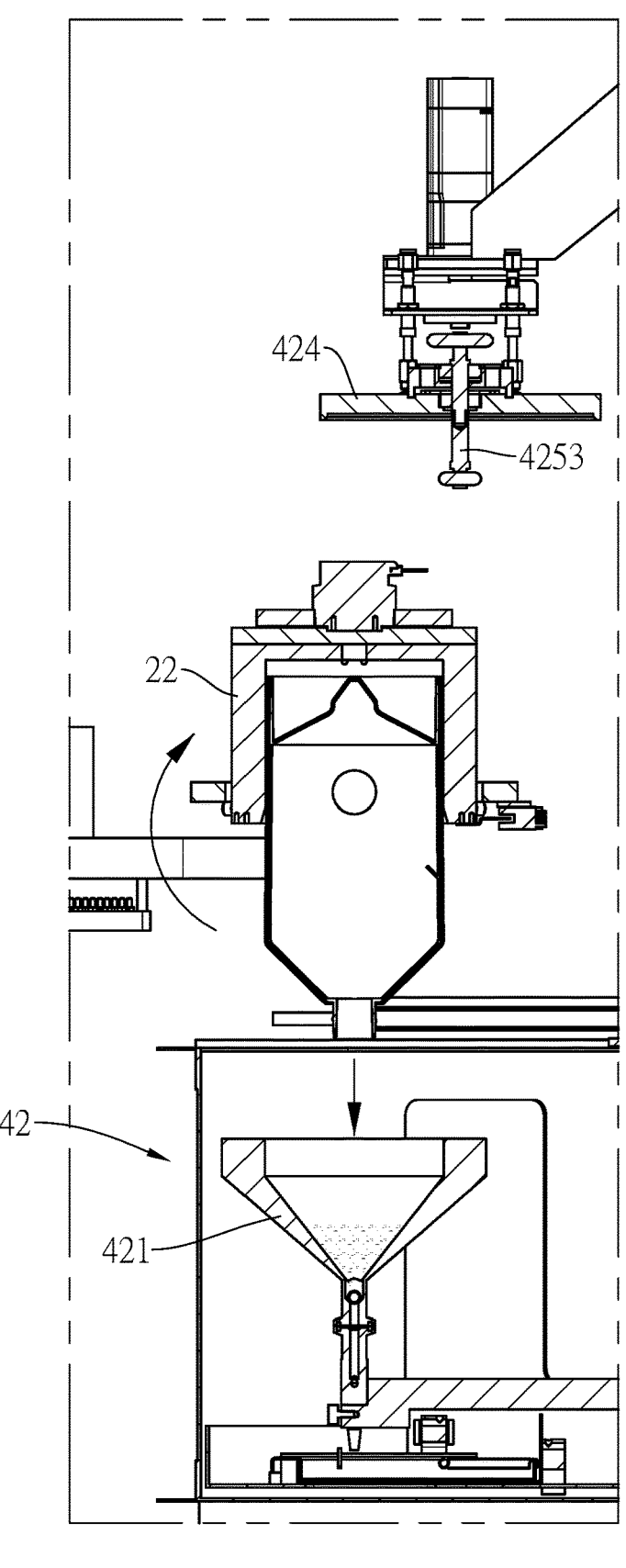

With reference to FIGS. 7, 21 and 22, each container holder 22 is configured to accommodate one of the cell culture containers 91 or one of the centrifuge containers 92. Each of the container holders 22 is pivotally mounted on the container-positioning table 21, and is pivotable to an emptying angle (as shown in FIG. 22) to empty contents in the culture container 91 or the centrifuge container 92. To be precise, each container holder 22 is mounted on the container-positioning table 21 via a shaft 221 and is pivotable around the shaft 221. The shaft 221 is preferably horizontal.

Figure 6:
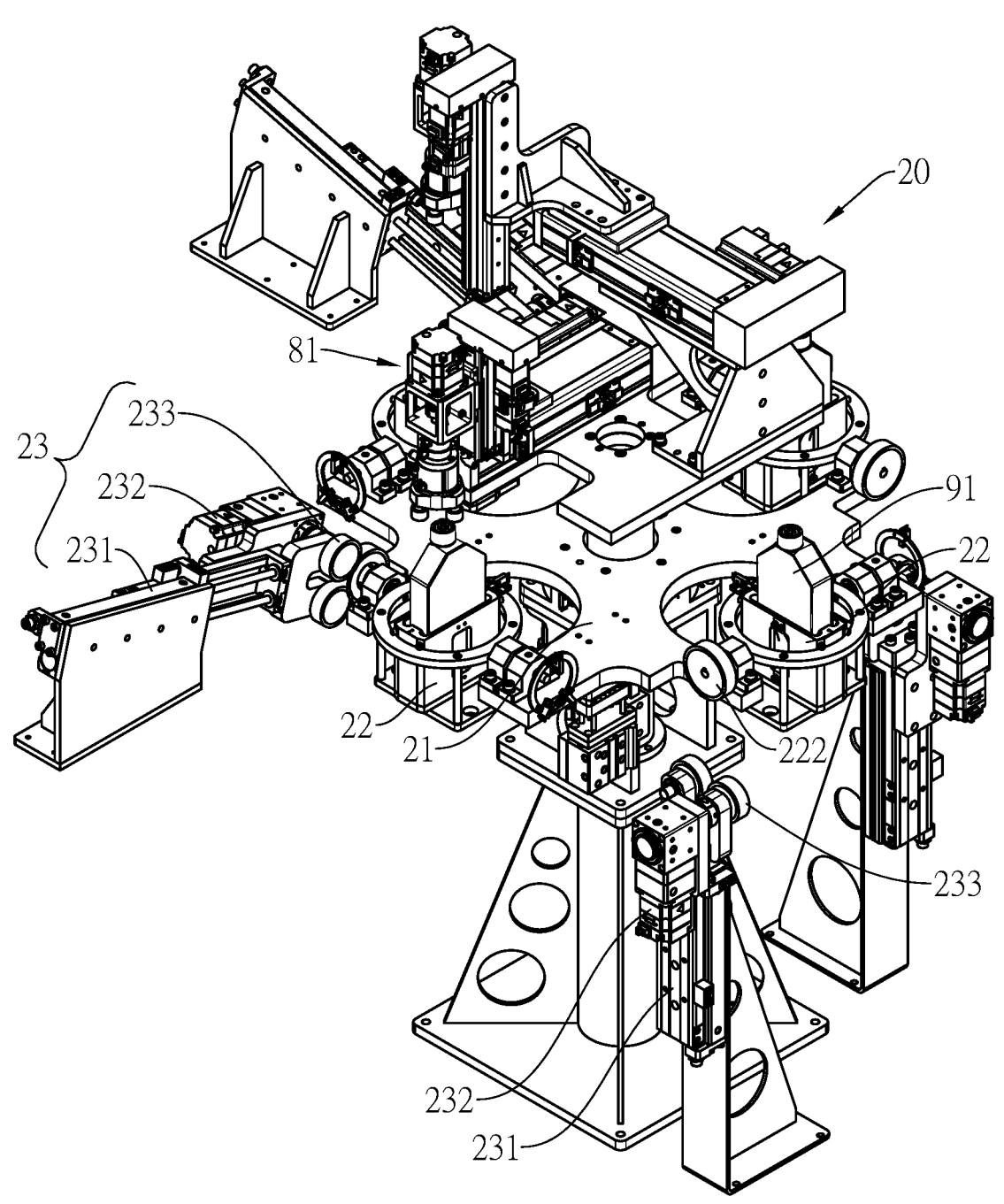
FIG. 6 is a perspective view of the container-handling device of the cell passaging device in FIG. 1.
Figure 13:
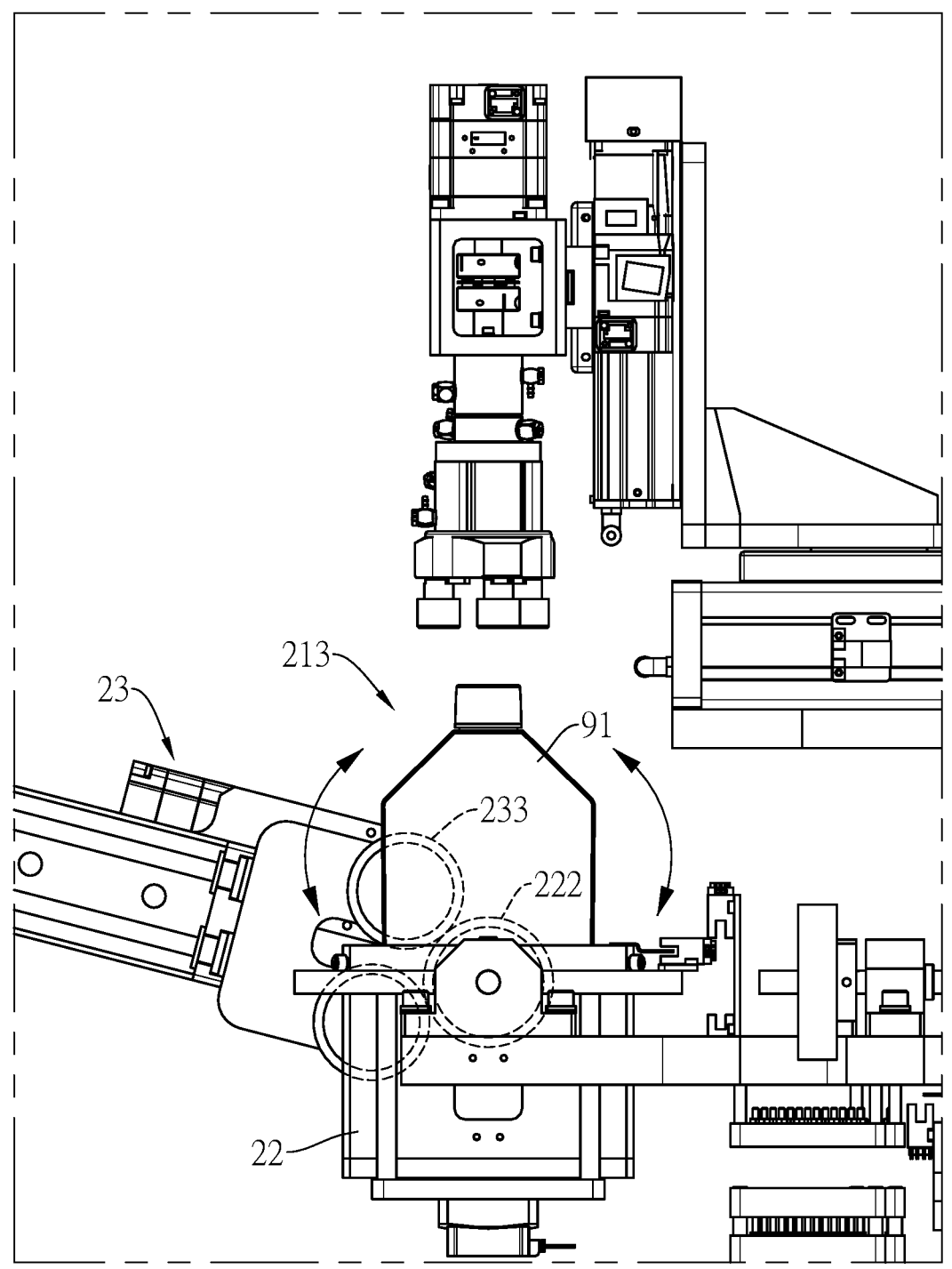
FIG. 13 is another enlarged side view of the cell passaging device in FIG. 1, showing the cell culture container being swayed by the container-handling device.

With reference to FIGS. 6, 7, and 13, a number of the container-driving assemblies 23 equals the number of the container holders 22. Each of the container-driving assemblies 23 controls an angle of a respective one of the container holders 22 and is configured to rotate the respective one of the container holders 22 to the emptying angle or to sway the respective one of the container holders 22.

In the preferred embodiment, each container-driving assembly 23 is mounted on the base and has a linear module 231, a motor 232, and one or multiple driving wheels 233. The linear module 231 is mounted on the base 10. The motor 232 and the driving wheels 233 are mounted on a slider of the linear module 231.

A position of said slider is controllable and the slider is configured to move toward the container holder 22 to make the driving wheels 233 abut against a driven wheel 222. The driven wheel 222 is connected to the shaft 221 such that the motor 232 can control the angle of the corresponding container holder 22 via the driving wheels 233 and the driven wheel 222. By mounting the container-driving assembly 23 on the base 10 instead of the container-positioning table 21, makes cabling of the linear module 231 and motor 232 more simplified.

Figure 3:
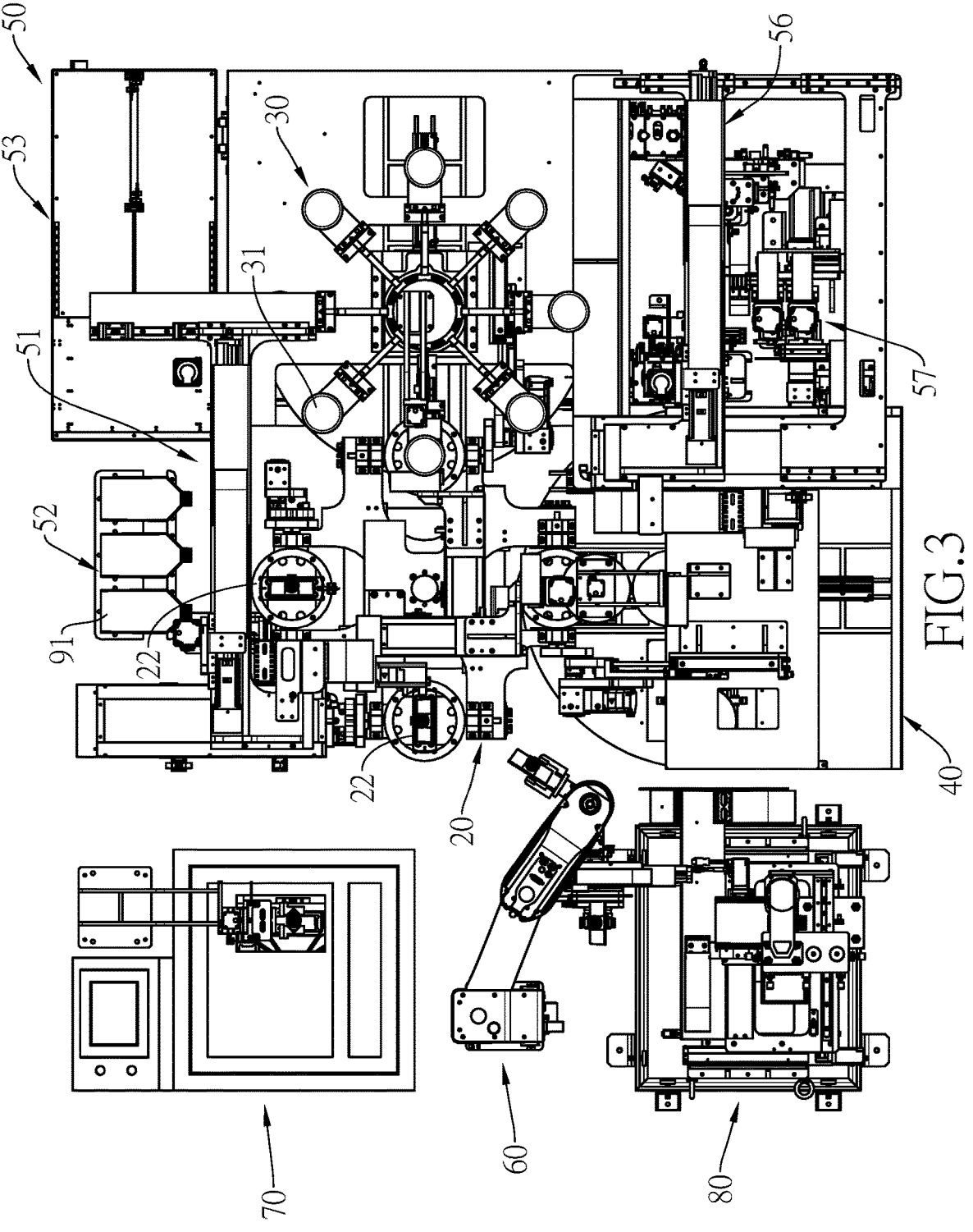
FIG. 3 is a top view of the internal structure of the cell passaging device in FIG. 2.
Figure 4:
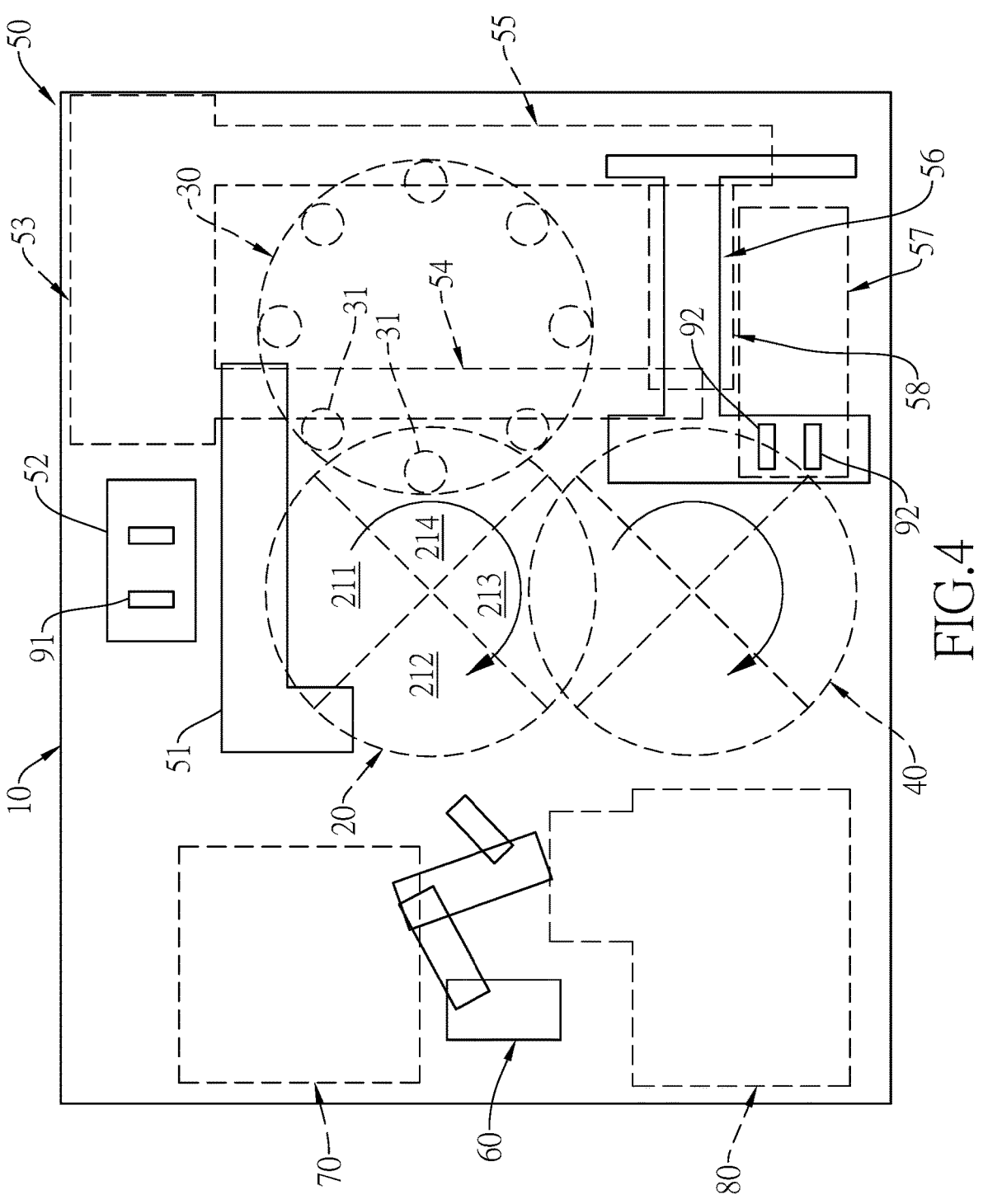
FIG. 4 is a simplified schematic top view of the internal structure of the cell passaging device in FIG. 3.
Figure 12:
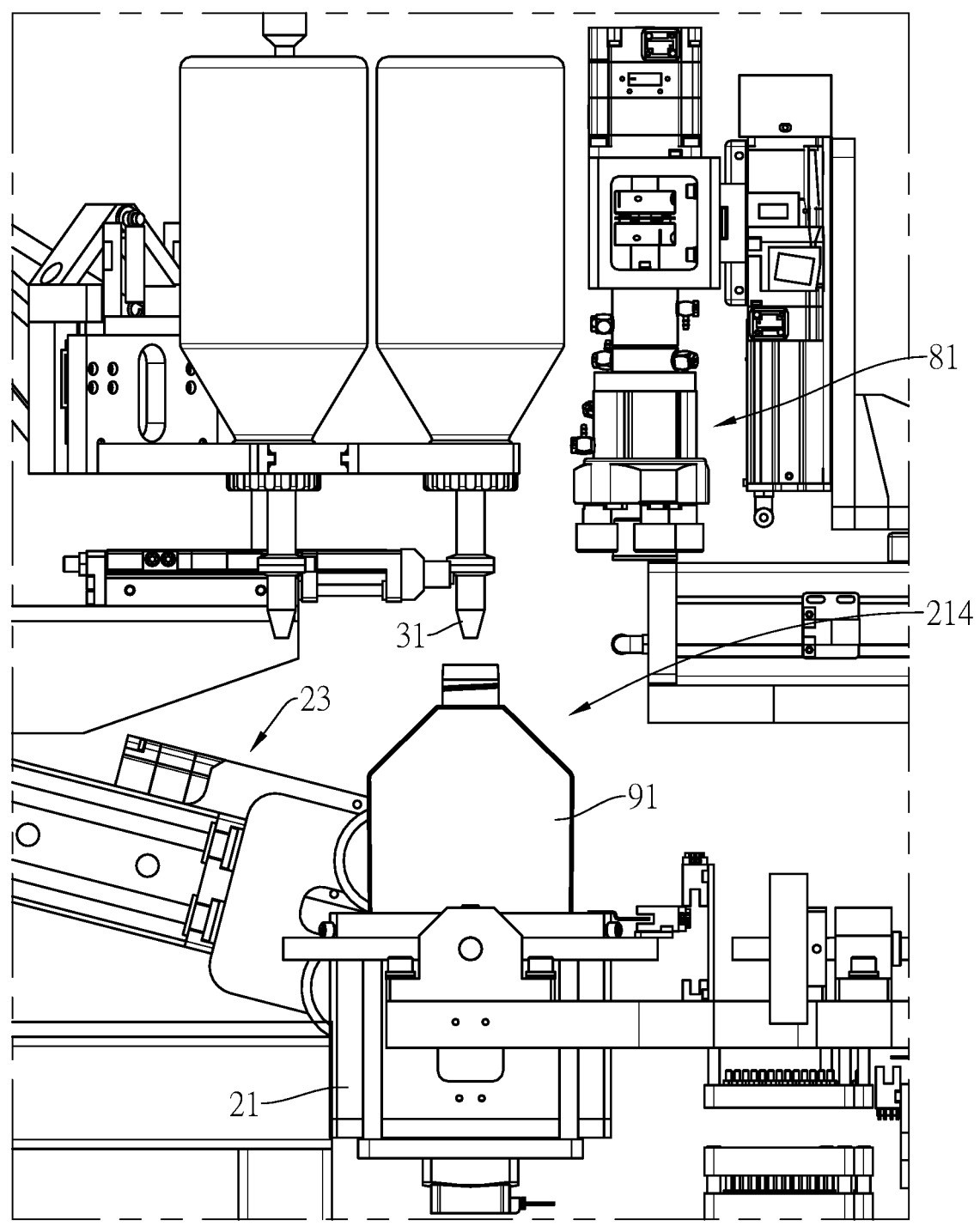
FIG. 12 is another enlarged side view of the cell passaging device in FIG. 1, showing an injection head of a liquid solution injection device aligned with the cell culture container.

With reference to FIGS. 3, 4, and 12, the liquid solution injection device 30 is mounted on the base 10 and has multiple injection heads 31. Each of the injection heads 31 is connected to a container with a kind of liquid solution and is movable to a position above the second injection position 214 to inject the liquid solution in a connected container into the cell culture container 91 located in the container holder 22 at the second injection position 214. The liquid solution injection device 30 is preferably disposed on a side, which is toward the second injection position 214, of the container-handling device 20.

In the preferred embodiment, the liquid solution injection device 30 is a turret. The injection heads 31 are disposed around a center axis of the turret and the turret is configured to rotate a specified injection head 31 to the position above the second injection position 214 for liquid solution injection. The liquid solutions connected to the injection head 31 include kinds of liquid reagents which can make adherent cells detach from a surface of the cell culture container 91, and also include balance reagent which can neutralize the effectiveness of the detaching reagent.

With reference to FIGS. 3, 4, 17 and 18, the liquid equal-splitting device 40 is disposed on a side of the container-handling device 20; the liquid equal-splitting device 40 has a funnel-positioning table 41 and at least one gravitational liquid-splitting device 42. The funnel-positioning table 41 is rotatably mounted on the base 10, and is preferably a conventional rotary indexing table.

The funnel-positioning table 41 is disposed lower in height than the container-positioning table 21, but disposed higher in height than the position of two centrifuge containers 92. One indexed position of the funnel-positioning table 41 is located under the first injection position 213 of the container-positioning table 21, and another indexed position of the funnel-positioning table 41 is located above the position of two centrifuge containers 92.

Figure 18:
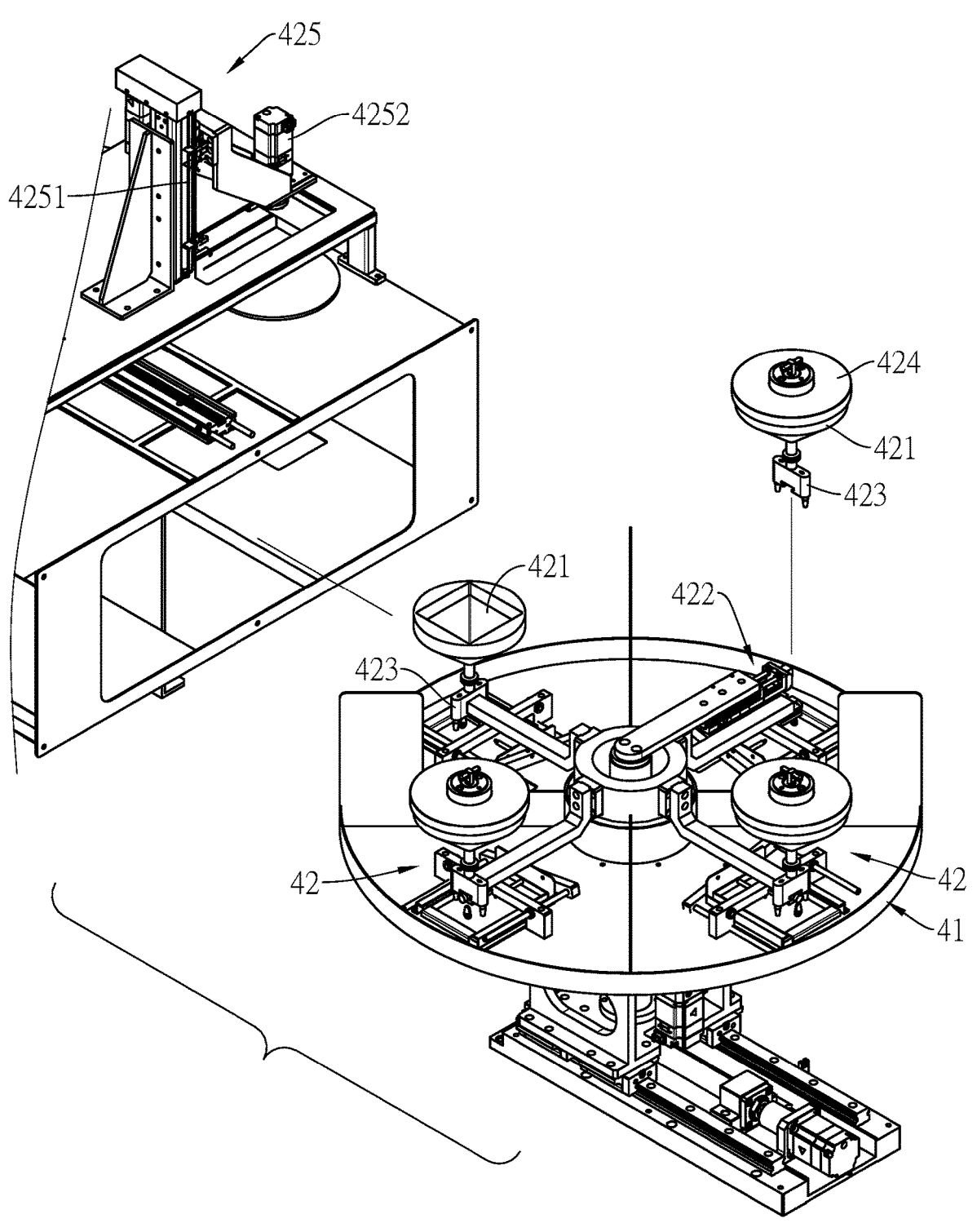
FIG. 18 is an exploded perspective view of the liquid equal-splitting device of the cell passaging device FIG. 17.
Figure 19:
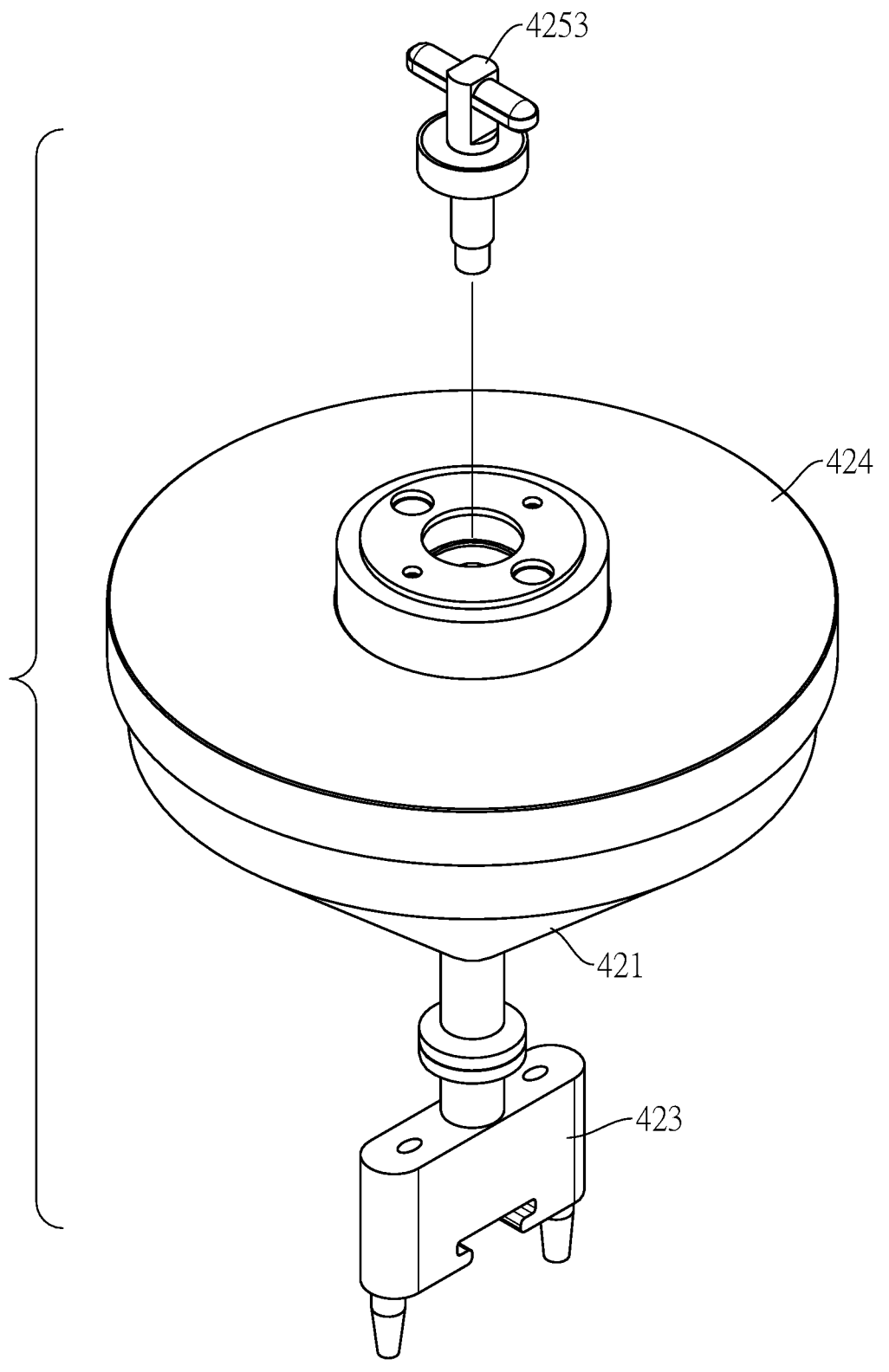
FIG. 19 is an exploded perspective view of a gravitational liquid-splitting device of the cell passaging device FIG. 18.
Figure 20:
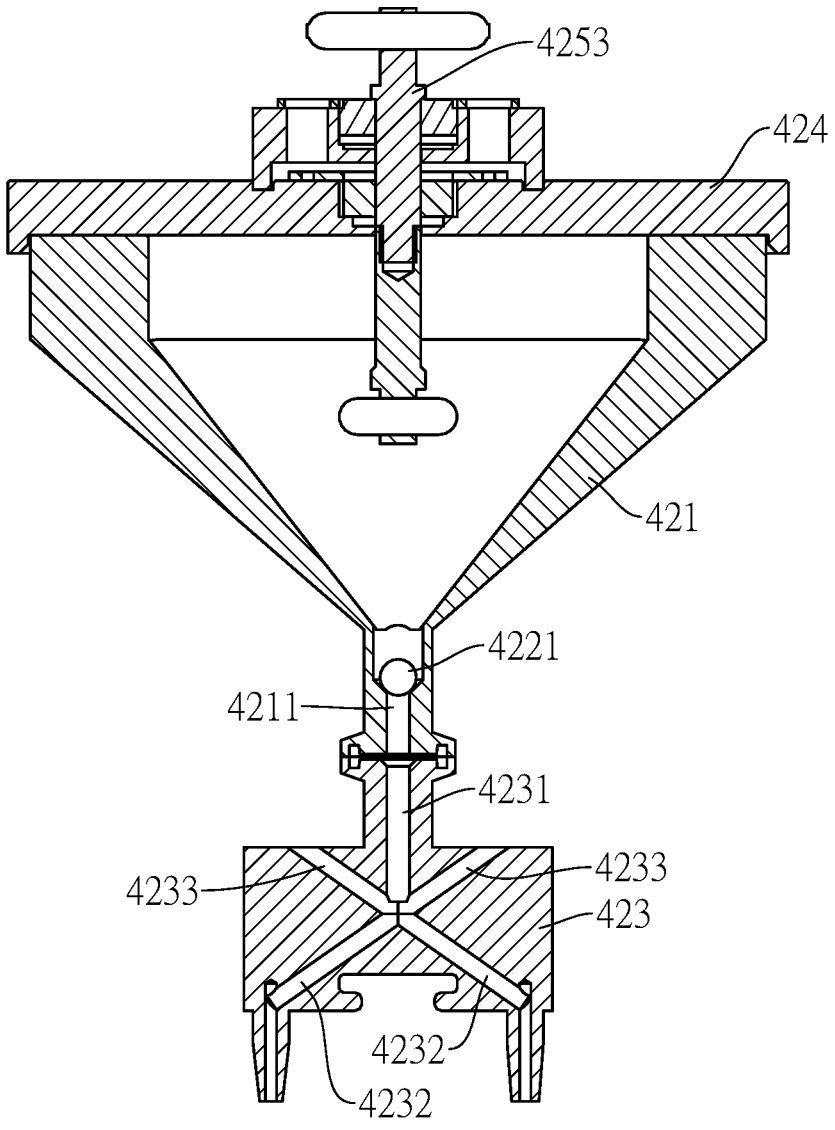
FIG. 20 is a sectional view of the gravitational liquid-splitting device of the cell passaging device FIG. 19, showing a first ferromagnetic part closing a bottom opening of a funnel.

With reference to FIGS. 18 to 20, the number of the gravitational liquid-splitting device 42 is preferably four, at least one, and the four gravitational liquid-splitting devices 42 are disposed around a center axis of the funnel-positioning table 41. Each gravitational liquid-splitting device 42 has a funnel 421, a dispensing valve 422, a liquid-splitting part 423, and a stirring assembly 425. In the preferred embodiment, each gravitational liquid-splitting devices 42 further has a funnel cover 424.

The funnel 421 has an inner space and a bottom opening, and the inner space is connected to the bottom opening. A first ferromagnetic part 4221 of the dispensing valve 422 is mounted in the funnel 421 and is configured to close or open the bottom opening of the funnel 421. Here "closing the bottom opening" means the dispensing valve 422 prevents liquid in the funnel 421 from flowing down via the bottom opening, and therefore the funnel 421 dispensing valve 422 does not have to directly cover the bottom opening.

In the preferred embodiment, the inner space of the funnel 421 forms a channel 4211 (as shown in FIG. 20) in the bottom of the funnel 421. The channel 4211 extends upward and downward, and a lower end of the channel 4211 forms the bottom opening of the funnel 421. The first ferromagnetic part 4221 of the dispensing valve 422 is disposed in the channel 4211 and is configured to be controlled to close or open the channel 4211, thereby closing or opening the bottom opening of the funnel 421.

With reference to FIGS. 20 to 23 and FIG. 25, the dispensing valve 422 has the first ferromagnetic part 4221, a valve actuator 4222, and a second ferromagnetic part 4223. The first ferromagnetic part 4221 is movably disposed in the channel 4211 of the funnel 421 and driven by a weight of the first ferromagnetic part 4221 to move toward the bottom opening of the funnel 421 to close the bottom opening (as shown in FIG. 20). The first ferromagnetic part 4221 is preferably a ball with a metal core.

Figure 25:
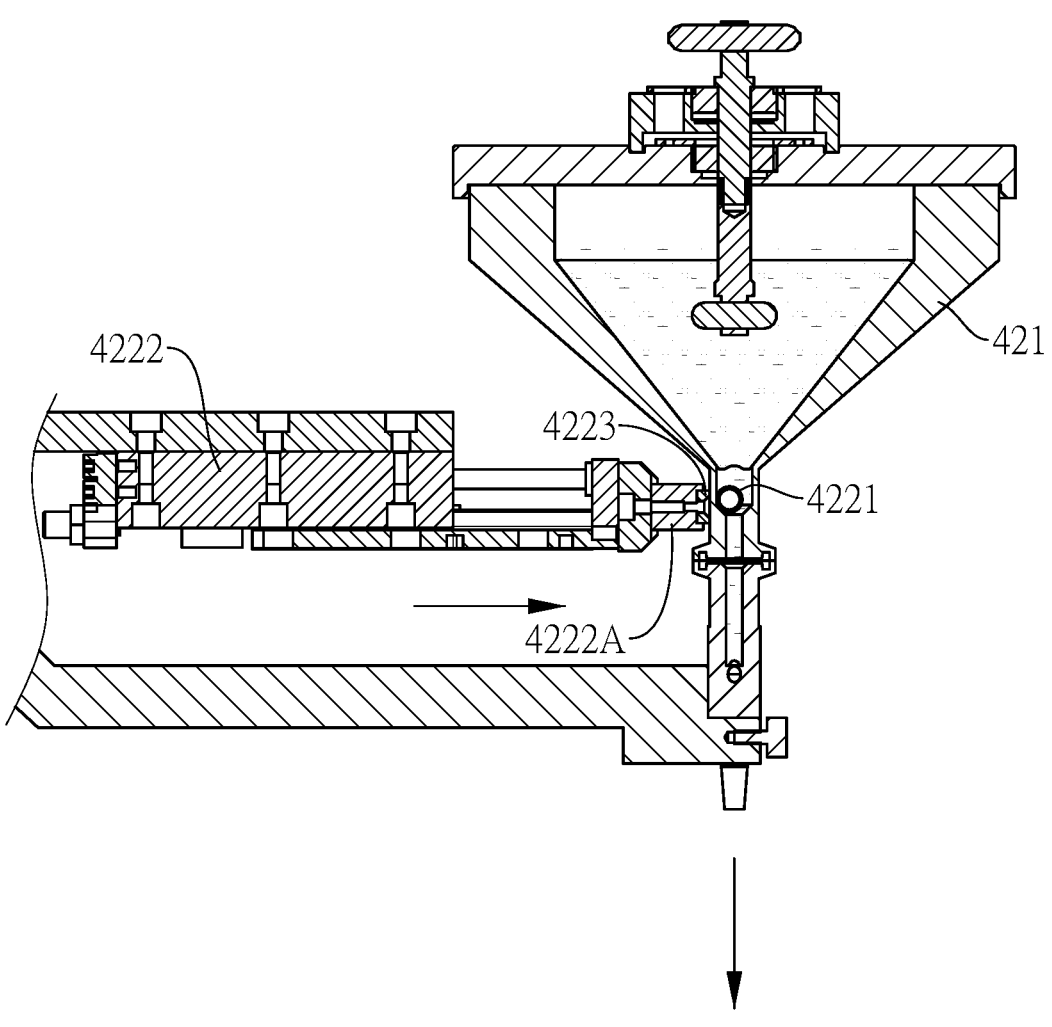
FIG. 25 is an enlarged sectional view of the cell passaging device in FIG. 1, showing a dispensing valve opening the bottom opening of the funnel.

The valve actuator 4222 is disposed outside of the funnel 421 and has a moving end 4222A which is controllable and configured to move toward the first ferromagnetic part 4221 to an open position (as shown in FIG. 25). To be precise, the valve actuator 4222 is a pneumatic cylinder. The valve actuator 4222 is mounted on the base 10 and can be controlled by pressurized air to make a slider of the valve actuator 4222 move toward the first ferromagnetic part 4221.

The second ferromagnetic part 4223 is mounted on a moving end 4222A of the valve actuator 4222. The second ferromagnetic part 4223 and the first ferromagnetic part 4221 magnetically attract or repel each other. When the moving end 4222A of the valve actuator 4222 is at the open position, the first ferromagnetic part 4221 is driven by the second ferromagnetic part 4223 to open the bottom opening of the funnel.

In the preferred embodiment, the second ferromagnetic part 4223 is a permanent magnet. When the moving end 4222A of the valve actuator 4222 is at the open position, the first ferromagnetic part 4221 is magnetically attracted by the second ferromagnetic part 4223 and opens the channel 4211. In another preferred embodiment (not shown in figures), the first ferromagnetic part 4221 and the second ferromagnetic part 4223 are permanent magnets which magnetically attract or repel each other, or the second ferromagnetic part 4223 is a coil which generates magnetic field when powered-on.

With reference to FIGS. 18 to 20, the liquid-splitting part 423 is connected to the bottom of the funnel 421. The liquid-splitting part 423 has an input channel 4231, two output channels 4232, and two auxiliary channels 4233 formed in the liquid-splitting part 423, but the auxiliary channels can be omitted.

The input channel 4231 extends upward and downward; an upper end of the input channel 4231 forms an input opening on a top of the liquid-splitting part 423 and connected to the bottom opening of the funnel. Each of the output channels 4232 has a first end and a second end; the first end is connected to a lower end of the input channel 4231; the second end extends inclinedly downward and connected to an exterior of the liquid-splitting part.

Liquid entering the input channel 4231 is split equally between the two output channels 4232 by gravity and shapes of the output channels 4232. In the preferred embodiment, each output channel 4232 is linear, and its lower end is connected to the exterior of the liquid-splitting part via a vertical channel.

Each auxiliary channel 4233 has a third end and a fourth end; the third end is connected to one of the two output channels 4232; the fourth end extends inclinedly upward and is connected to the exterior of the liquid-splitting part. To be specific, each auxiliary channel 4233 extends along a same straight line with a respective one of the output channels 4232.

Function of the auxiliary channels 4233 is to balance pressure in the two output channels 4232, thereby stabilizing flow speed in the two output channels 4232. Therefore, the auxiliary channels 4233 further ensure the liquid entering the input channel 4231 is split equally between the two output channels 4232. Moreover, each auxiliary channel 4233 is in line with a respective one of the output channels 4232 for ease of cleaning. In another preferred embodiment, there is only one auxiliary channel 4233, and the third end of the auxiliary channel 4233 is connected to both of the two output channels 4232.

With reference to FIGS. 18, 20, 23, and 24, the funnel cover 424 detachably covers an upper opening of the funnel 421. The stirring assembly 425 has a linear module 4251, a stirring motor 4252, and a stirrer 4253. The linear module 4251 is mounted on the base 10 and can be controlled to move a slider 4251A of the linear module 4251. The stirring motor 4252 is mounted on the slider 4251A of the linear module 4251. The stirrer 4253 is rotatably mounted through the funnel cover 424 and is configured to stir liquid in the funnel 421.

Figure 24:
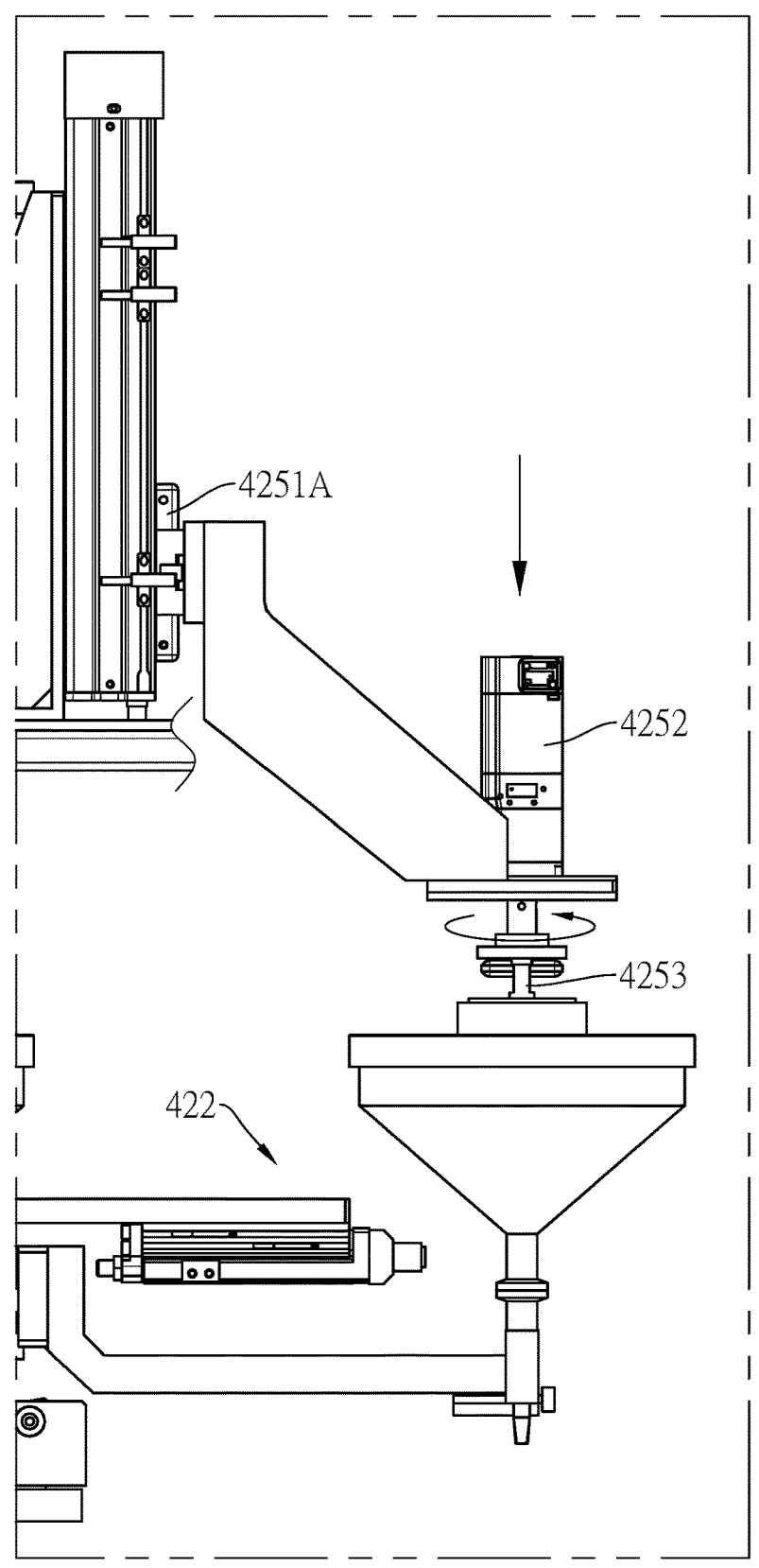

When the funnel cover 424 covers the funnel 421, the linear module 4251 is configured to move the stirring motor 4252 toward the stirrer 4253 (as shown in FIG. 24) such that an output axle of the stirring motor 4252 is connected to an upper end of the stirrer 4253, thereby allowing the stirring motor 4252 to rotate the stirrer 4253. Structure of the stirring assembly 425 is not limited by the abovementioned as long as there is a stirrer 4253 configured to stir liquid in the funnel 421.

With reference to FIGS. 3, 4, 18, and 20, rotation of the funnel-positioning table 41 is configured to move each of the gravitational liquid-splitting devices 42 from a position under the first injection position 213 to a position above the position of two centrifuge containers 92 such that liquid in the funnel 421 of each gravitational liquid-splitting device 42 flows into the two centrifuge containers 92 via the two output channels 4232 respectively.

In the preferred embodiment, the funnel-positioning table 41 is both rotatable on a horizontal plane and linearly movable toward or away from the container-handling device 20. The funnel-positioning table 41 moves each gravitational liquid-splitting device 42 to the position above the two centrifuge containers 92 by a combination of said rotation and linear motion.

Operation mode of the funnel-positioning table 41 is not limited to rotation. In another preferred embodiment, the funnel-positioning table 41 moves the gravitational liquid-splitting devices 42 along a straight line or a bent line to move the gravitational liquid-splitting devices 42 among multiple specific positions.

With reference to FIGS. 2 to 4 and FIG. 28, the primary container-moving device 50 is configured to move each of the two centrifuge containers 92 from the position under the gravitational liquid-splitting device 42 to the container holder 22 at the container-receiving position 211.

Additionally, the primary container-moving device 50 is also configured to move the cell culture container 91 in the container holder 22 at the container-receiving position 211 to the position under the gravitational liquid-splitting devices 42 such that liquid in the funnel 421 of the corresponding gravitational liquid-splitting device 42 flows into the cell culture container 91. Therefore, the primary container-moving device 50 allows the present invention to recycle two of the cell culture containers 91 so that they can be used again as the two centrifuge containers 92.

In the preferred embodiment, the primary container-moving device 50 has a first multi-axis transfer mechanism 51, a container rack 52, a first conveyer 53, a second conveyer 54, a third conveyer 55, a second multi-axis transfer mechanism 56, and a bottling and transferring mechanism 57.

With reference to FIG. 5 and FIGS. 8 to 10, the first multi-axis transfer mechanism 51 is preferably a three-axis transfer mechanism which includes three linear modules 511. One of the linear modules 511 that extends vertically has a gripper 512 mounted on a lower end of said linear module 511. The gripper 512 is configured to grip one of the containers (e.g., the cell culture container 91 or the centrifuge container 92) accommodated in the container holder 22 at the container-receiving position 211, the container rack 52, or the first conveyer 53. The gripper 512 is also configured to put the gripped container in any one of the said three components. To be more precise, the gripper 512 is configured to rotate 90 degrees along a horizontal axis to change an angle of the gripped container.

The container rack 52 is configured to accommodate twelve containers to improve operational efficiency. The first conveyer 53 includes a translating mechanism and an elevating mechanism such that the first conveyer 53 moves containers from a bottom to a top of the first conveyer 53 where the first multi-axis transfer mechanism 51 can grip the container or put several new containers in the container rack 52 one by one.

The second conveyer 54 and the third conveyer 55 are linear belt conveyors. One end of each conveyor is mounted in a bottom of the first conveyer 53, and another end of each conveyor extends to the second multi-axis transfer mechanism 56.

The second multi-axis transfer mechanism 56 is preferably a three-axis transfer mechanism which is configured to move containers among the second conveyer 54, the third conveyer 55, and the bottling and transferring mechanism 57.

Figure 26:
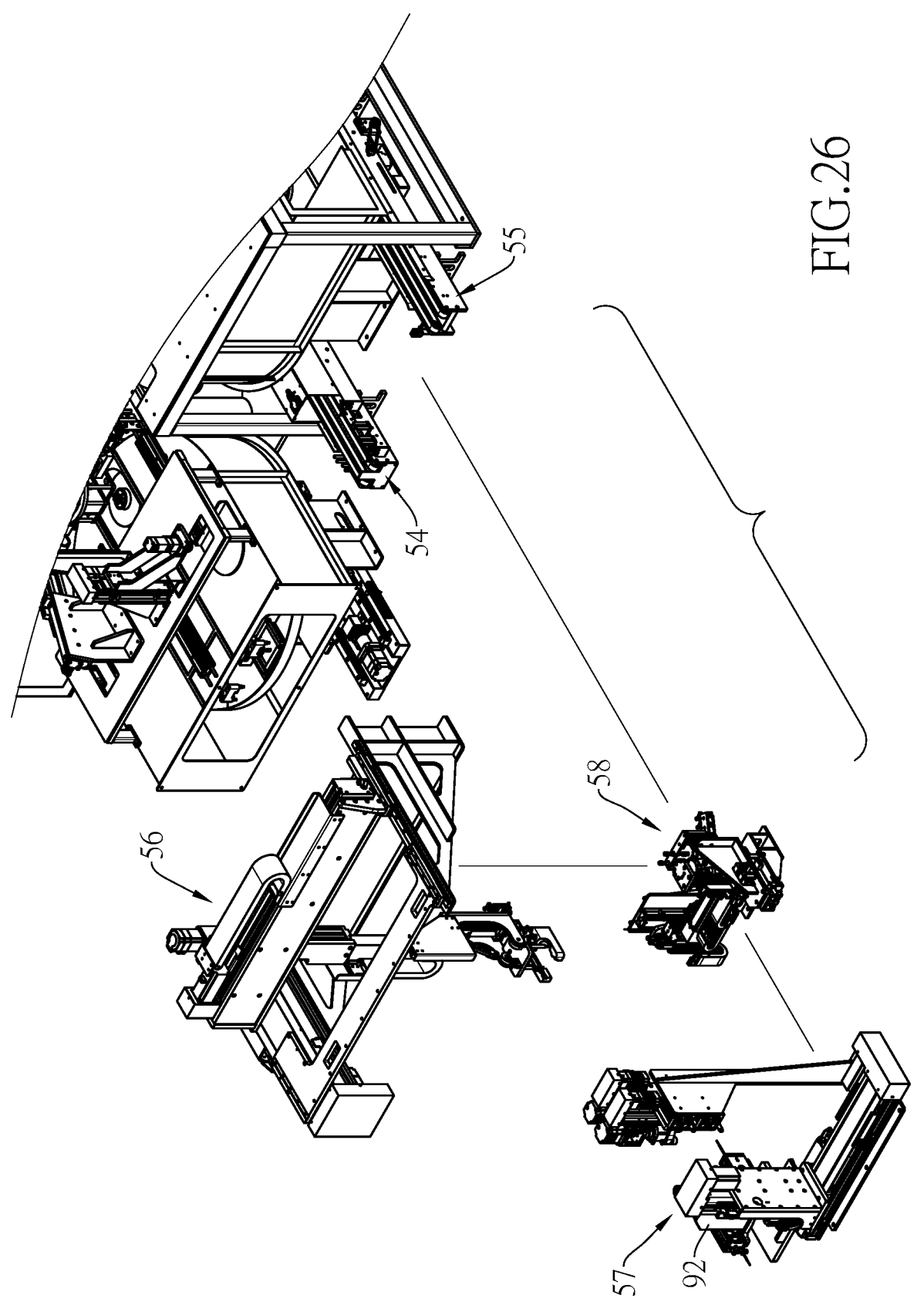
FIG. 26 is another enlarged exploded perspective view of the cell passaging device in FIG. 1.
Figure 27:
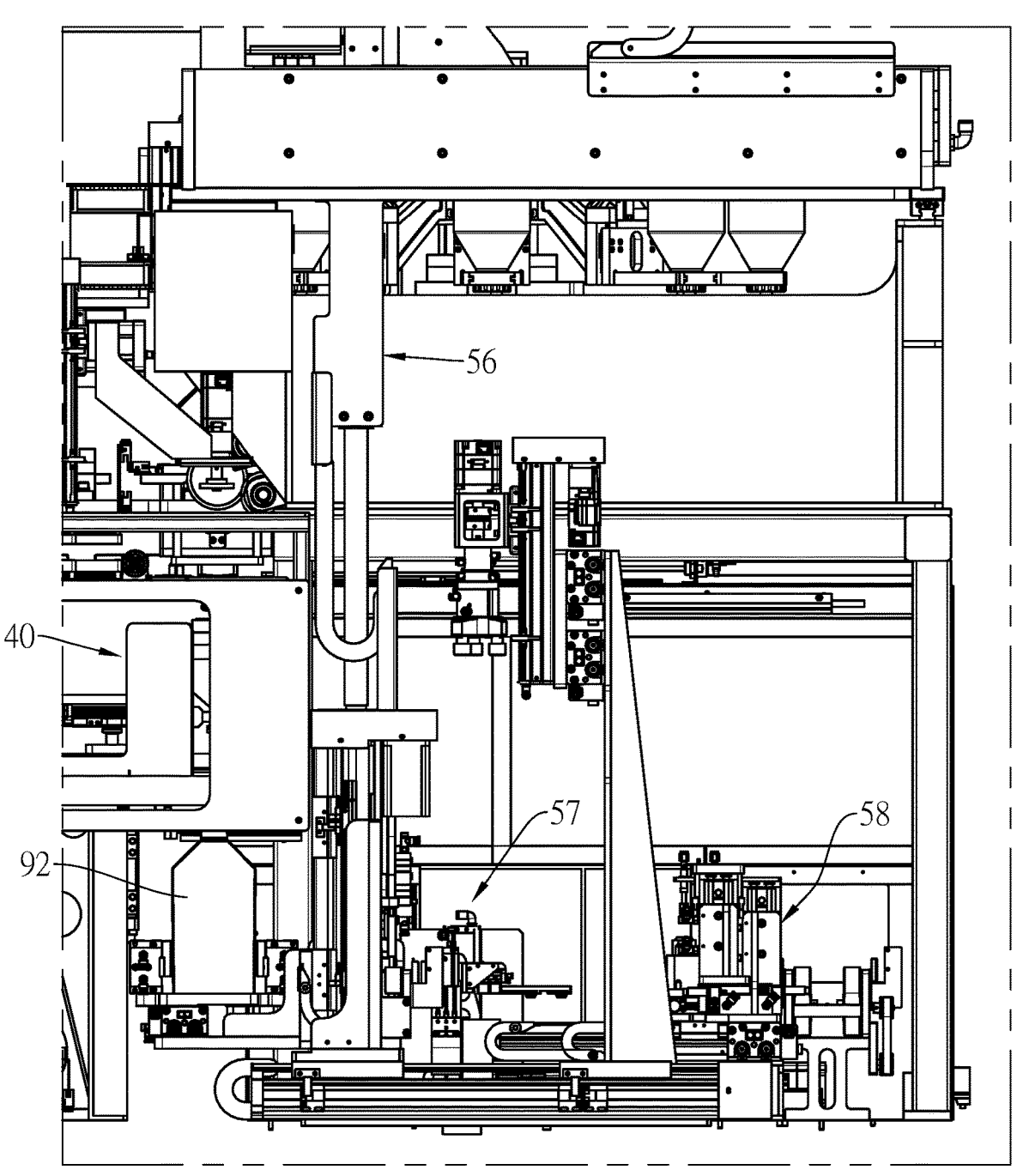
FIG. 27 is another enlarged side view of the cell passaging device in FIG. 1.
Figure 28:
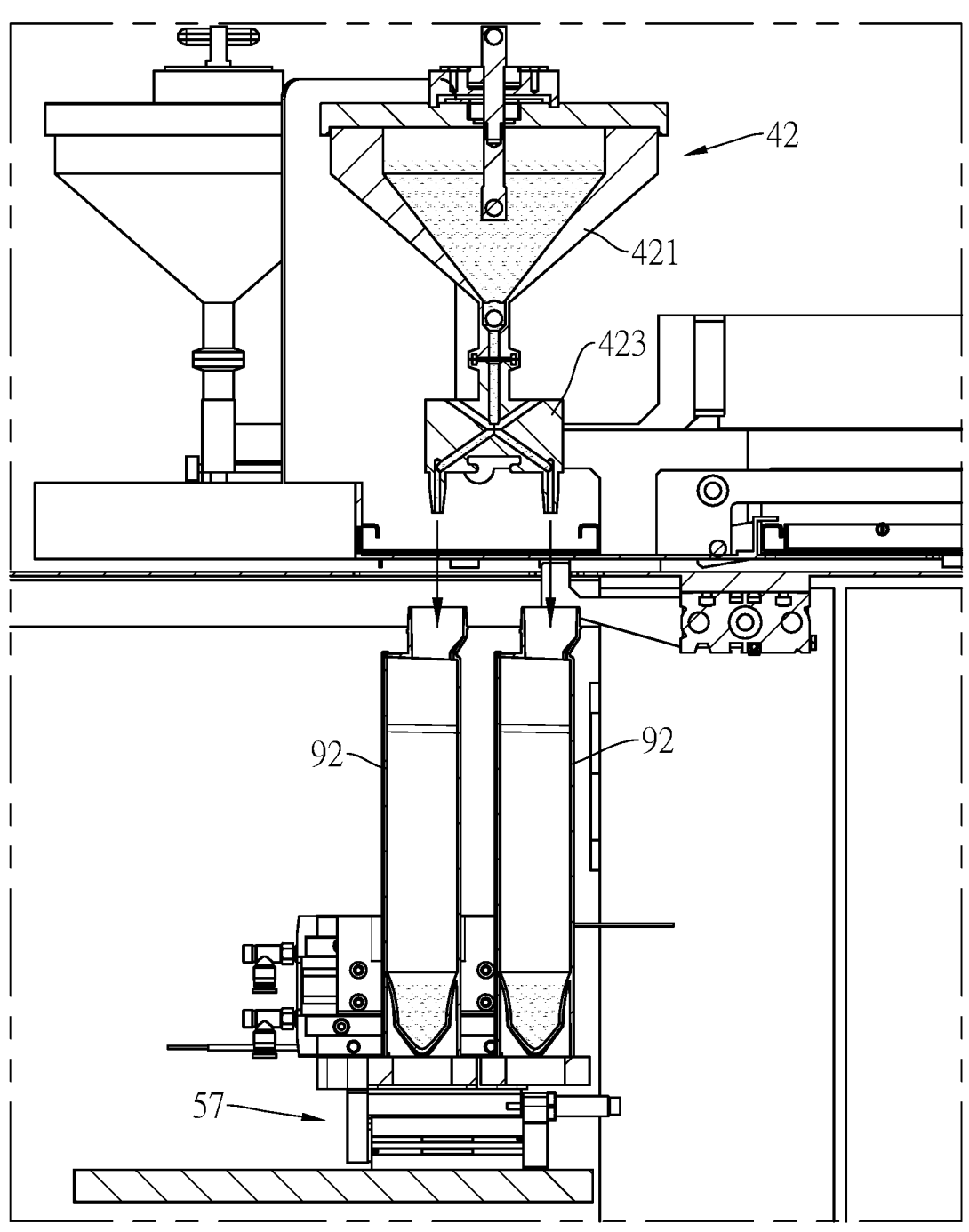
FIG. 28 is another enlarged sectional view of the cell passaging device in FIG. 1, showing contents in the gravitational liquid-splitting device being split equally and flowing downward to two centrifuge containers thereunder.

With reference to FIGS. 26 to 28, the bottling and transferring mechanism 57 is configured to grip the double centrifuge containers 92, double the cell culture containers 91, double cryovials (not shown in figures), double cell solution containers (not shown in figures), or other types of containers. The bottling and transferring mechanism 57 is configured to align the two gripped containers with the two output channels 4232 of one of the gravitational liquid-splitting devices 42 such that the liquid in said gravitational liquid-splitting device 42 can be transferred to the two gripped containers. After transferring the liquid, the bottling and transferring mechanism 57 moves the two gripped containers away from the position under the container-positioning table 21 for the second multi-axis transfer mechanism 56 to grip for the further operation.

In the preferred embodiment, a cell solution container cap mechanism 58 is disposed under the second multi-axis transfer mechanism 56. The cell solution container cap mechanism 58 is configured to handle caps of the cell solution containers in collaboration with the second multi-axis transfer mechanism 56.

Figure 2:
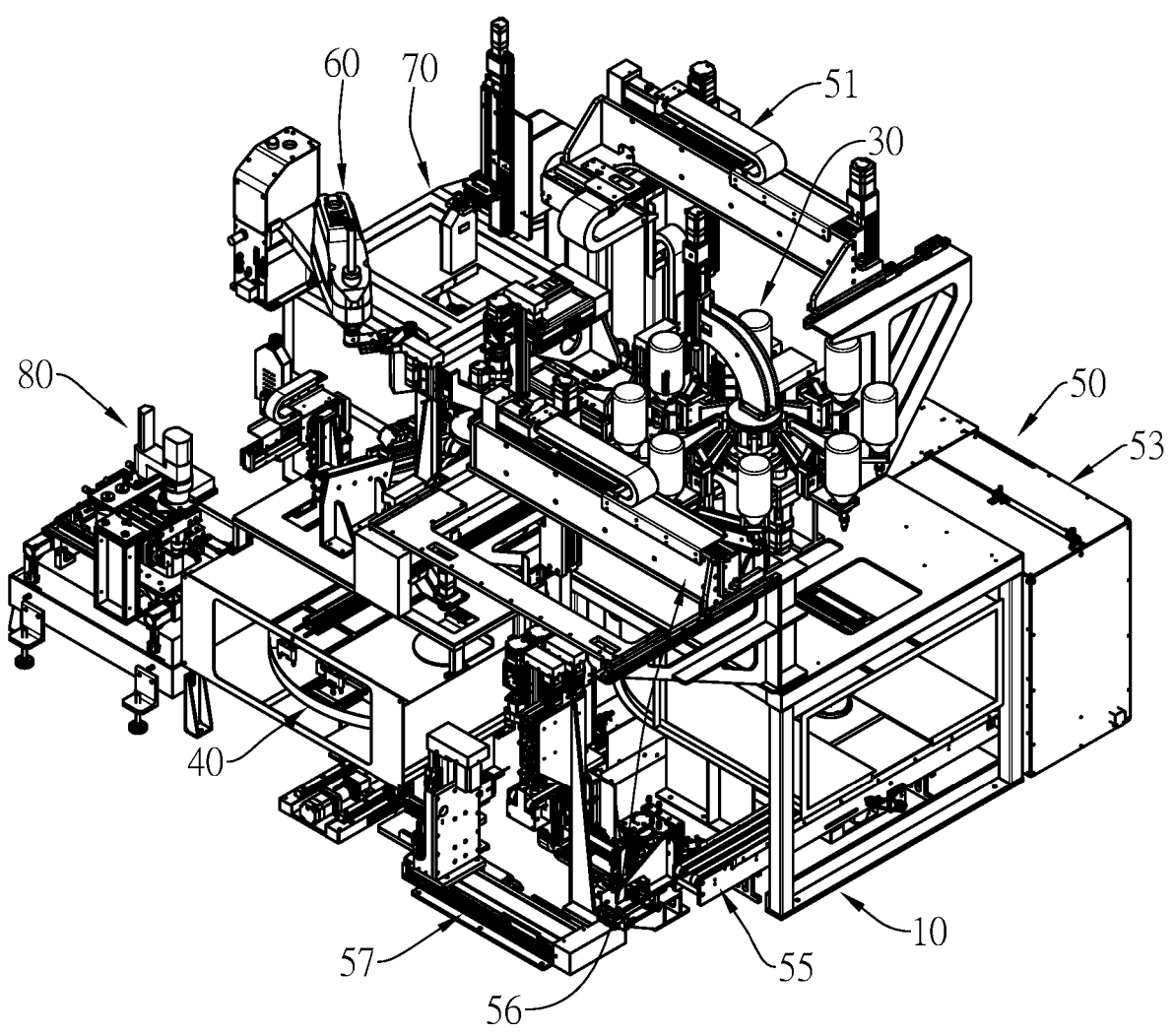
FIG. 2 is another perspective view of the cell passaging device in FIG. 1, showing an internal structure of the cell passaging device.

With reference to FIGS. 2 to 4, the auxiliary container-moving device 60, the centrifuge 70, and the optical inspection device 80 are disposed on a same side of the container-handling device 20 as where the container output position 212 is. The centrifuge 70 and the optical inspection device 80 are standardized conventional equipment. The optical inspection device 80 is configured to measure a number of cells in the culture container 91 in order to determine whether a total number of the cells collected in the culture container 91 is satisfactory for the further cell passaging process. To be more specific, the optical inspection device 80 is configured to calculate automatically the number of detached cells in the cell culture containers 91 by a specific AI algorithm.

Figure 14:
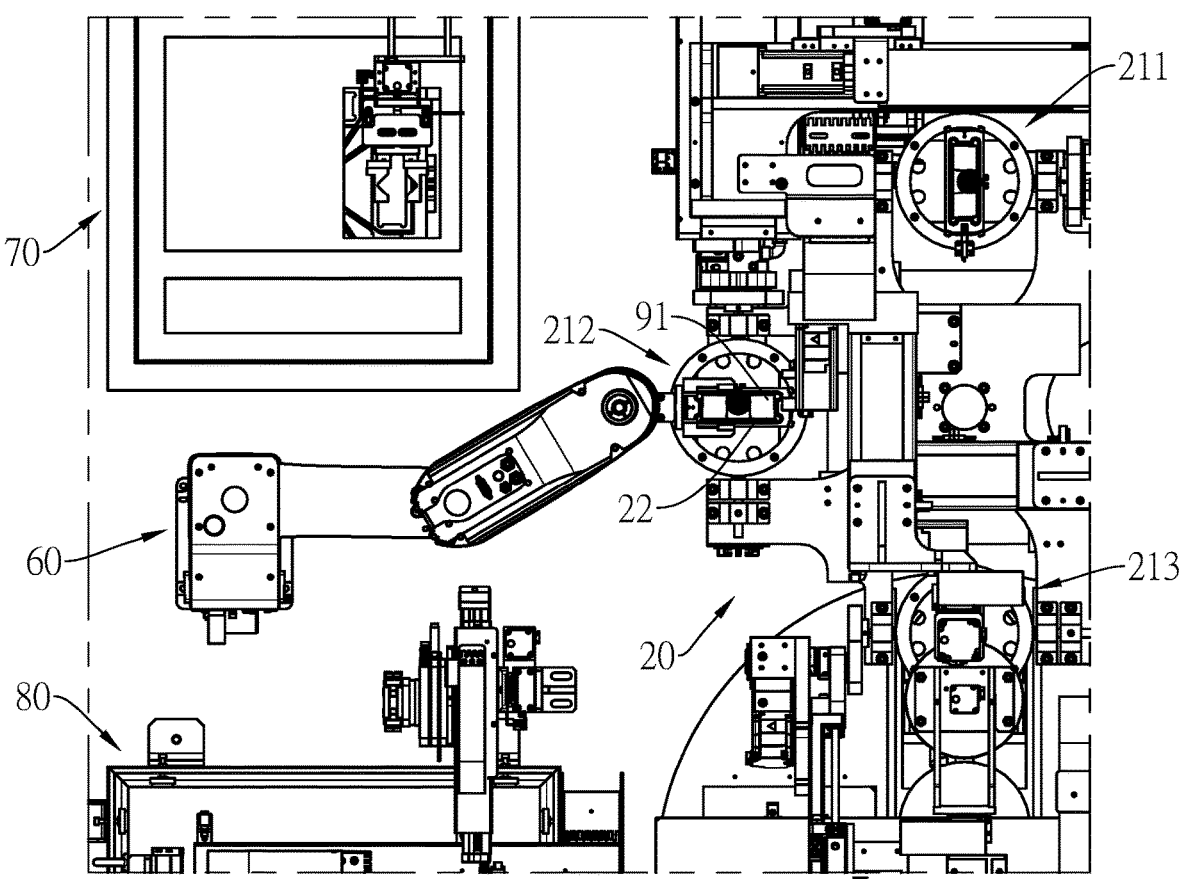
FIGS. 14 to 16 are enlarged schematic top views of the cell passaging device in FIG. 1, showing an auxiliary container-moving device moving the cell culture container in a container output position, to a centrifuge, or to an optical inspection device.
Figure 15:
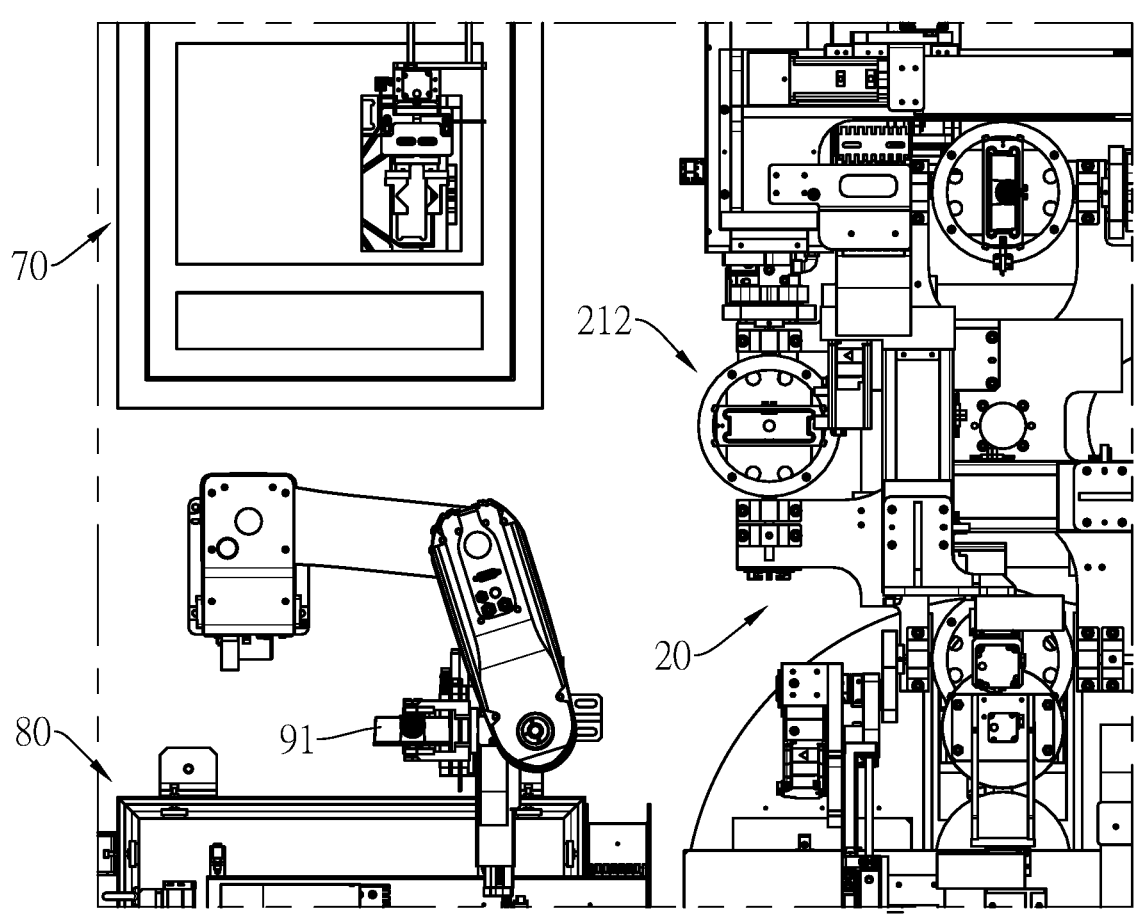
Figure 16:
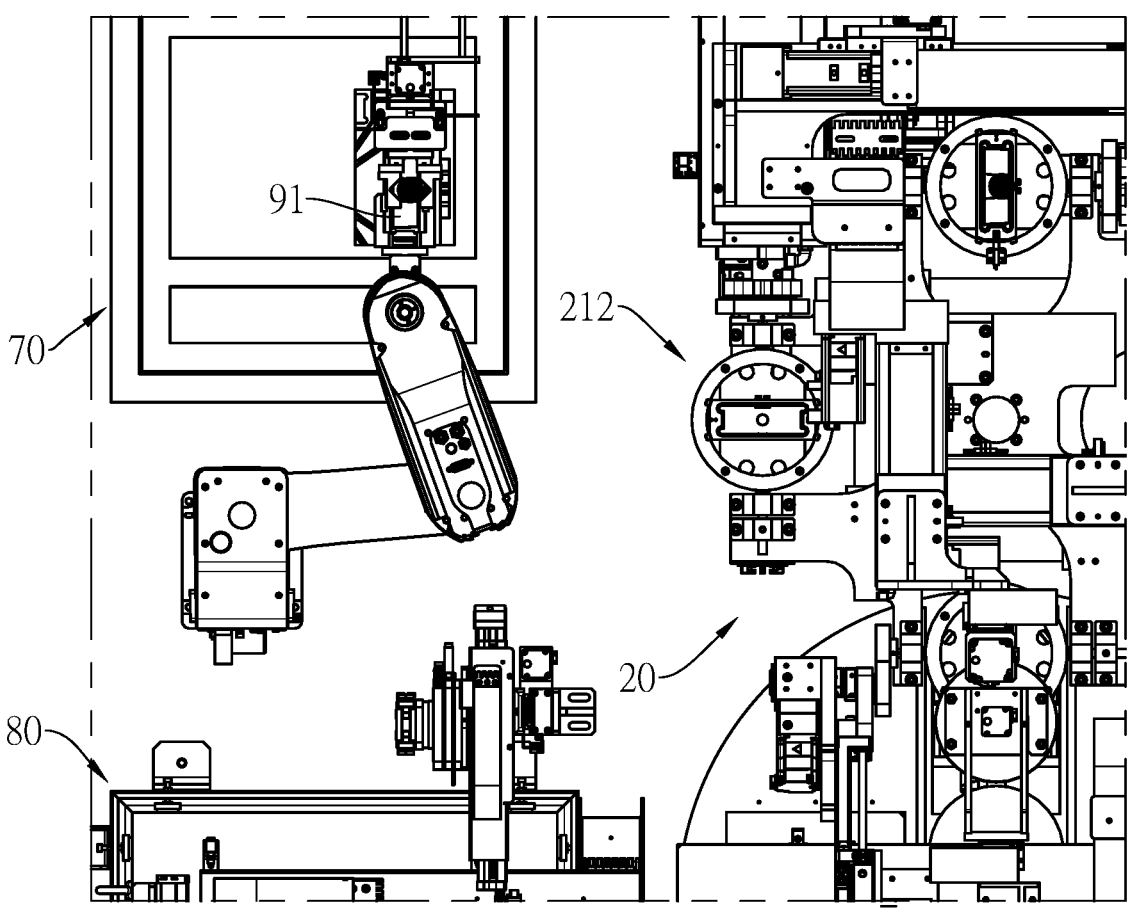
Figure 17:
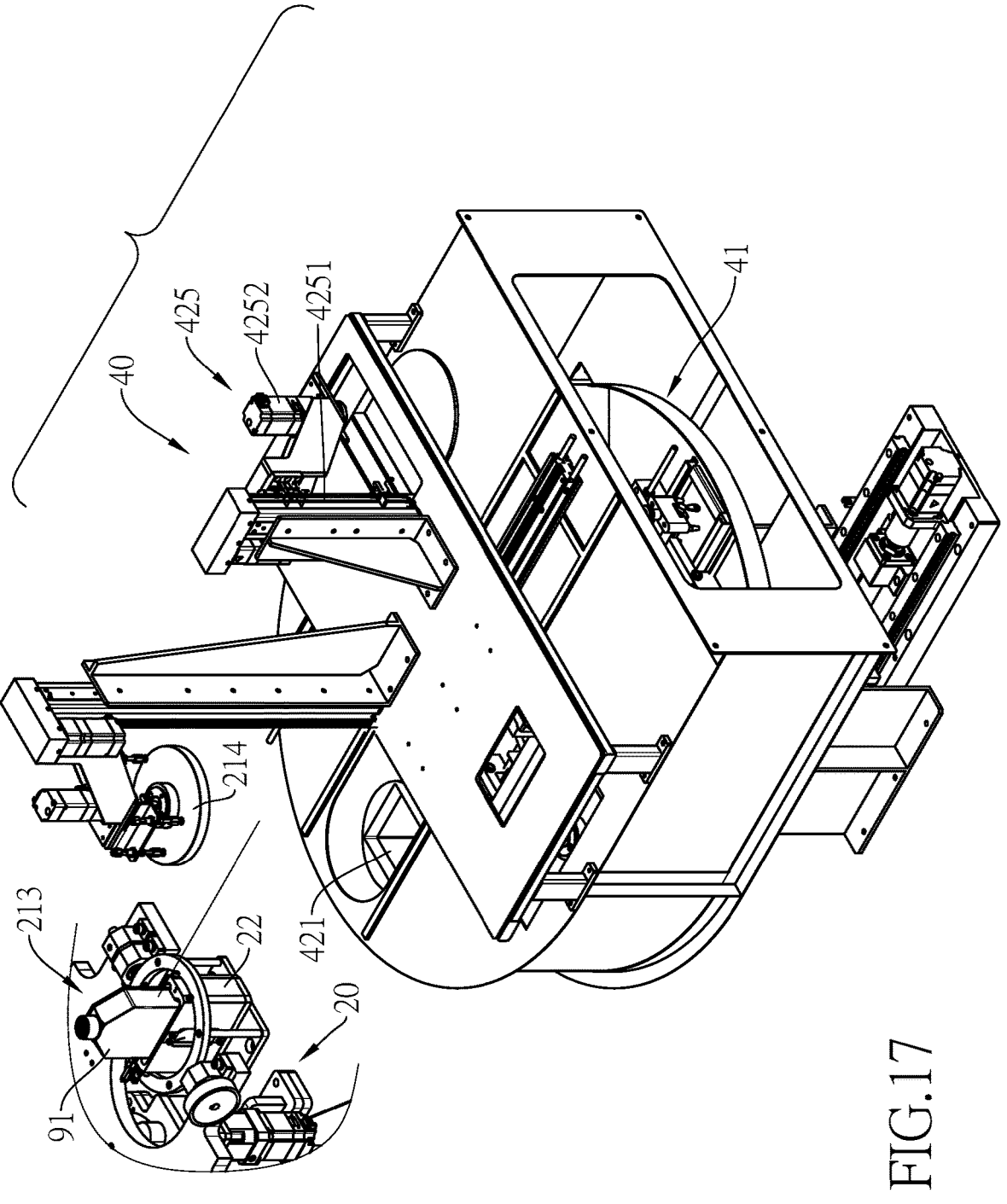
FIG. 17 is an enlarged exploded perspective view of the cell passaging device in FIG. 1, showing a liquid equal-splitting device.

With reference to FIGS. 14 to 16, the auxiliary container-moving device 60 is configured to move the centrifuge container 92 or the cell culture container 91 in the container holder 22 at the container output position 212 into the centrifuge 70, and also configured to move the centrifuge container 92 or the cell culture container 91 in the centrifuge 70 back into the container holder 22 at the container output position 212.

Additionally, the auxiliary container-moving device 60 is configured to move the centrifuge container 92 or the cell culture container 91 in the container holder 22 at the container output position 212 into the optical inspection device 80, and also configured to move the centrifuge container 92 or the cell culture container 91 in the optical inspection device 80 back into the container holder 22 at the container output position 212. The auxiliary container-moving device 60 is preferably a robotic arm.

The cell passaging method in accordance with the present invention is preferably performed using the abovementioned cell passaging device. The cell passaging device is configured to automatically perform various cell passaging methods for cell subculture process. One of the cell passaging methods for subculture of adherent cells, which is in accordance with the present invention, is explained below.

Figure 5:
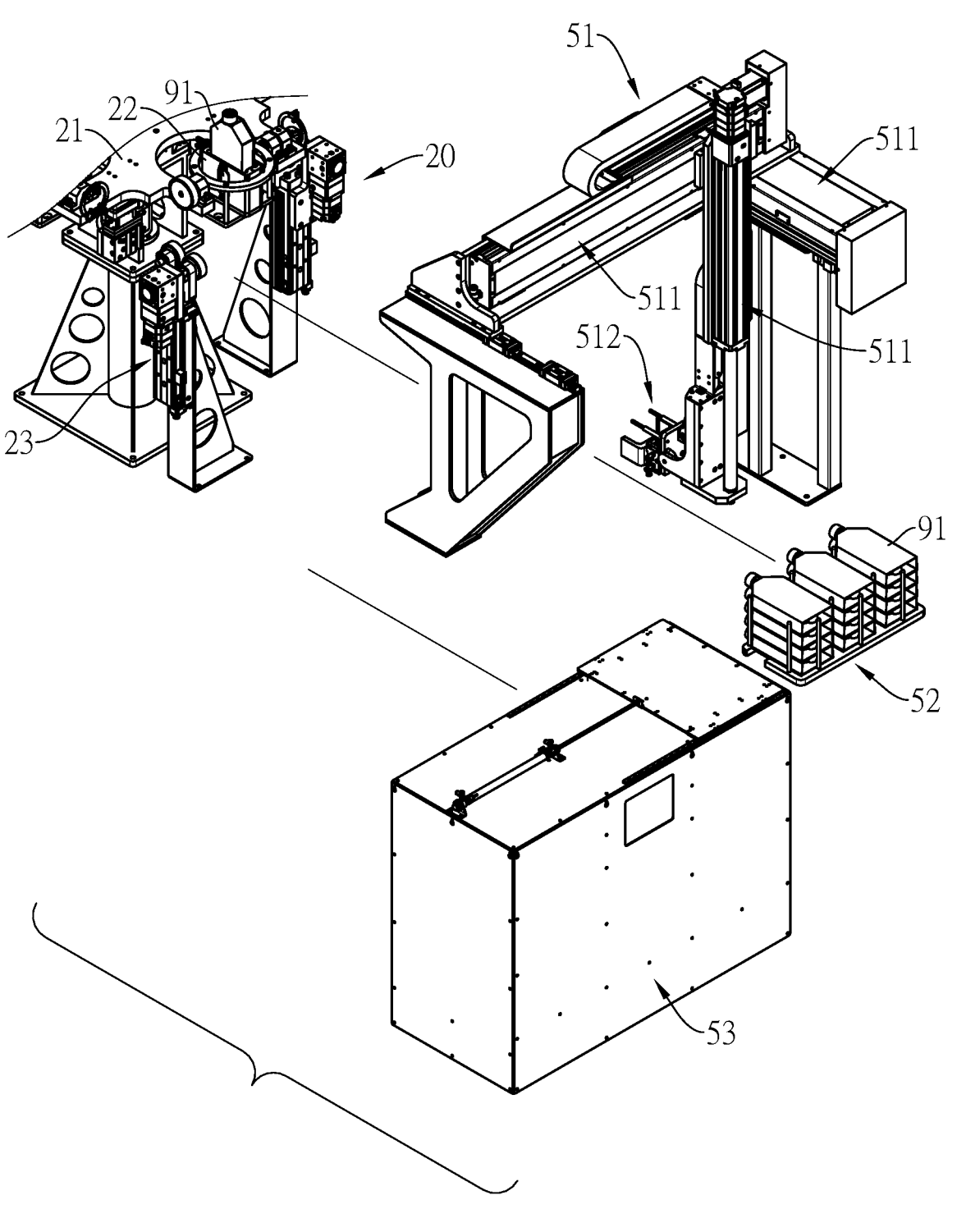
FIG. 5 is an exploded perspective view of a container-handling device and a primary container-moving device of the cell passaging device in FIG. 1.

With reference to FIGS. 3 to 5, multiple cell culture containers 91 already in the stationary phase are transmitted to the first conveyer 53 of the primary container-moving device 50 by an external transfer mechanism.

Figure 8:
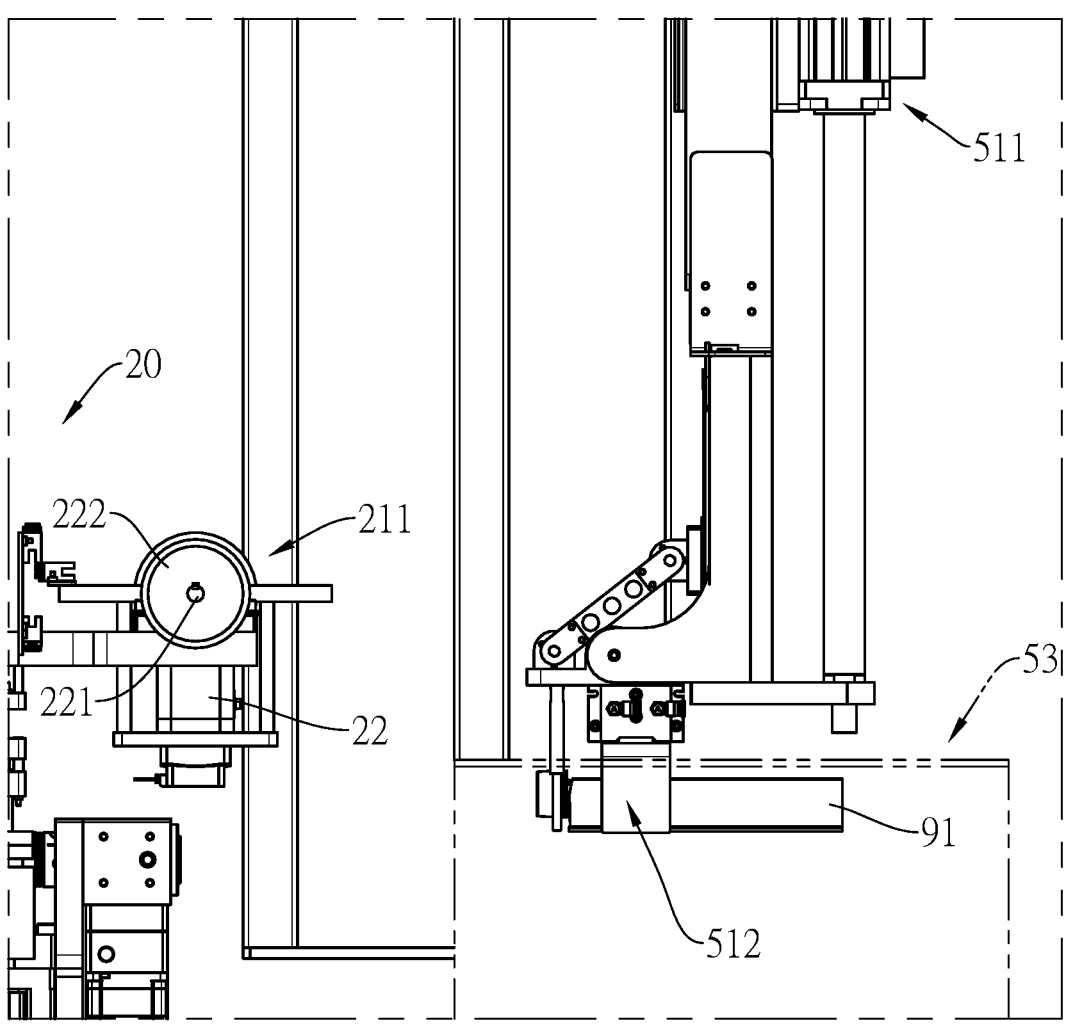
FIGS. 8 to 10 are enlarged side views of the cell passaging device in FIG. 1, showing a first multi-axis transfer mechanism of the primary container-moving device moving a cell culture container to a container-handling device.
Figure 9:
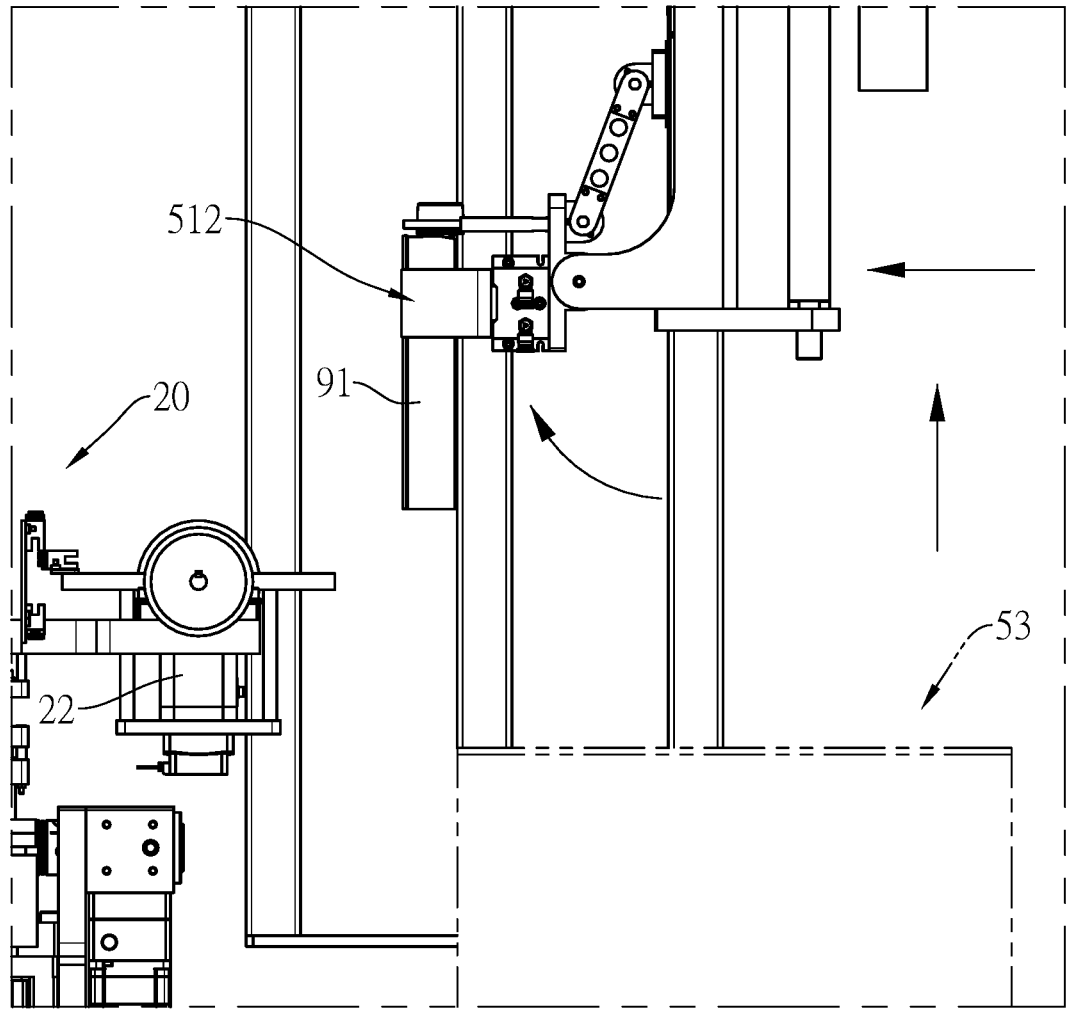
Figure 10:
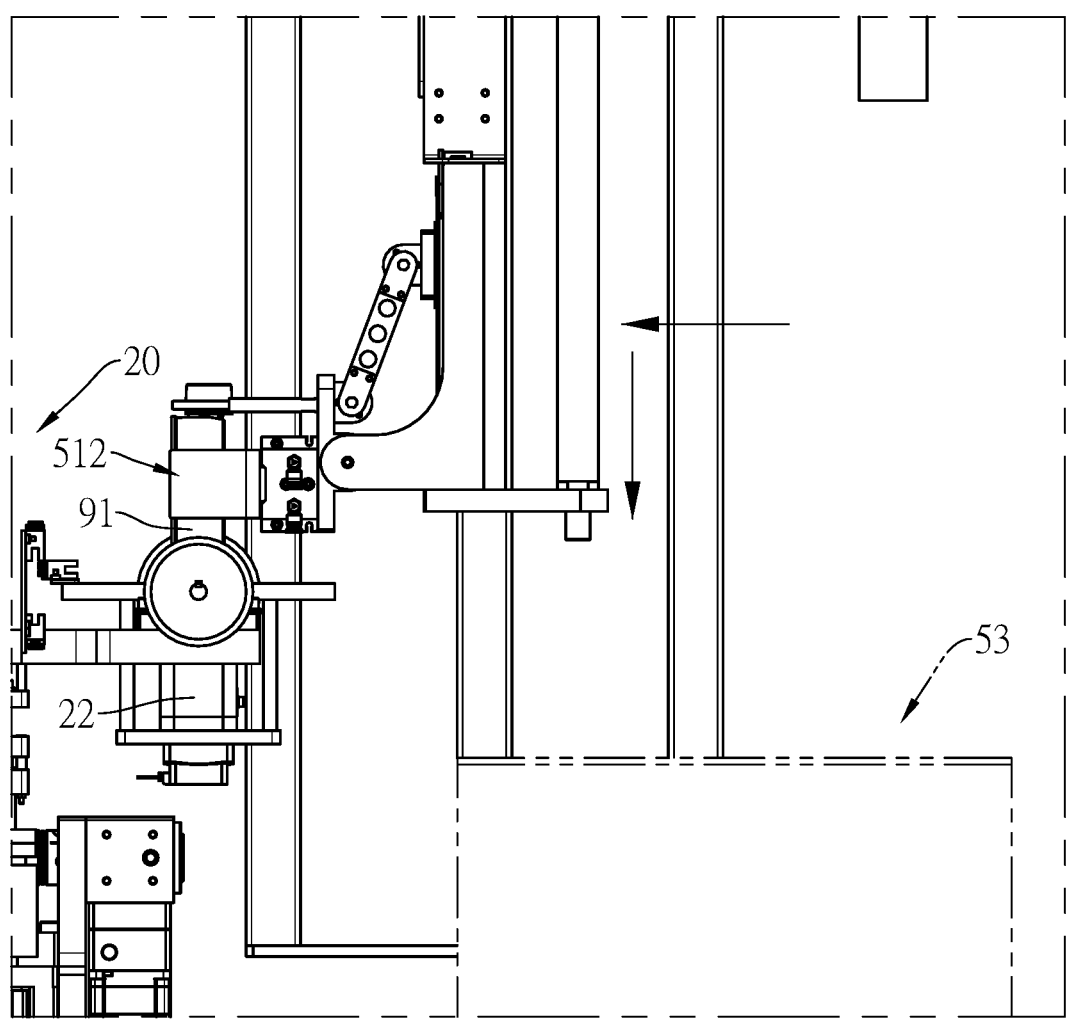

With reference to FIGS. 8 to 10, then, the first multi-axis transfer mechanism 51 grips the cell culture containers 91 in the first conveyer 53 and dispenses the cell culture containers 91 into the container holder 22 at the container-receiving position 211. The gripper 512 of the first multi-axis transfer mechanism 51 rotates the gripped cell culture container 91 from a horizontal posture to a vertical posture (as shown in FIGS. 8 and 9) before putting the gripped cell culture container 91 into the container holder 22 for ease of subsequent operation.

Figure 11:
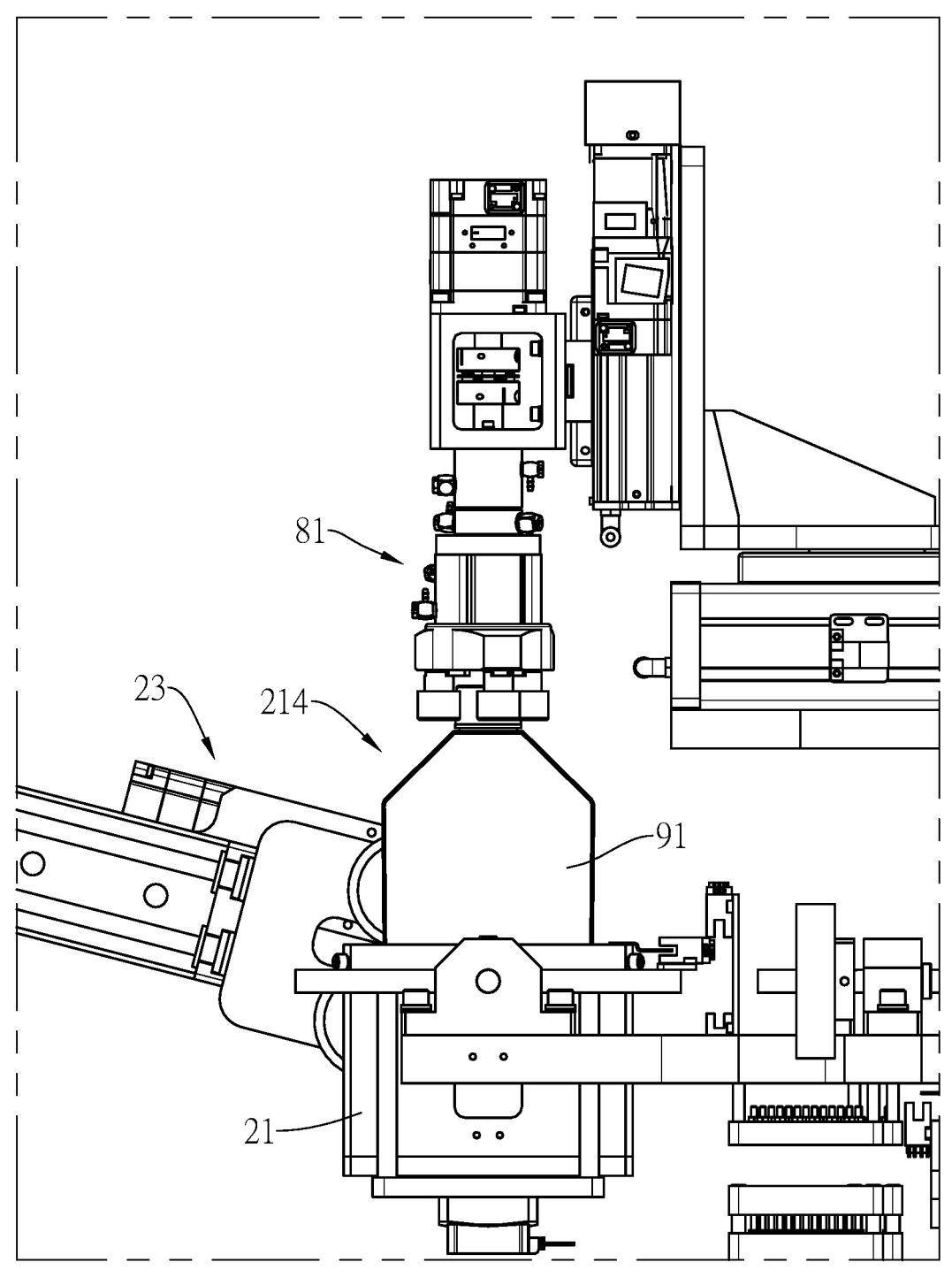
FIG. 11 is another enlarged side view of the cell passaging device in FIG. 1, showing a cap mechanism moving down and gripping a cap of a cell culture container.

With reference to FIGS. 4 and 11, then, the cell culture container 91 is moved from the container-receiving position 211 to the second injection position 214. A cap mechanism 81 moves down to grip a cap of the cell culture container 91.

With reference to FIG. 12, then, a cap mechanism 81 loosens the cap of the cell culture container 91 and moves the cap aside, and the container-driving assembly 23 rotates the container holder 22 to empty the content (ex. medium) of the cell culture container 91. Then, the injection head 31 of the liquid solution injection device 30 moves to the position above the second injection position 214 and injects the detaching reagent (ex. Trypsin) into the cell culture container 91, wherein the detaching reagent is functioned to make the adherent cells detach from the surface of the cell culture container 91.

With reference to FIGS. 4 and 13, then, the cap mechanism 81 puts the cap back onto the cell culture container 91 and tightens the cap, and the culture container 91 is moved to the first injection position 213. The container-driving assembly 23 sways the culture container 91 at the first injection position 213 to make cells detached from the surface of the cell culture container 91.

With reference to FIGS. 14 and 15, then, the cell culture container 91 is moved to the container output position 212, and then the auxiliary container-moving device 60 grips the cell culture container 91 and dispenses the culture container 91 into the optical inspection device 80 to calculate automatically the number of cells in the cell culture container 91 by using a specific AI algorithm.

When the process of cell counting in the optical inspection device 80 has finished, the culture cell container 91 is moved back to the container output position 212, and subsequently moved to the second injection position 214. At the second injection position 214, another one of the injection heads 31 of the liquid solution injection device 30 injects balance reagent into the cell culture container 91 to neutralize the effectiveness of detaching reagent.

With reference to FIGS. 4, 21, and 22, then, the culture cell container 91 is moved to the first injection position 213, and the container-driving assembly 23 rotates the container holder 22 to pour contents (e.g., solution with detached cells) in the cell culture container 91 into the funnel 421 of the gravitational liquid-splitting device 42. The funnel cover 424 on top of the funnel 421 has been removed before this step. Then, the above steps are performed again for the rest of the cell culture containers 91 until the solutions with detached cells from all culture containers 91 are collected in the funnel 421.

Among the cell culture containers 91, the first two cell culture containers 91 are moved to the position under one of the gravitational liquid-splitting devices 42 after their solutions with detached cells are poured into the funnel 421 such that the first two cell culture containers 91 serve as the two centrifuge containers 92.

Figure 23:
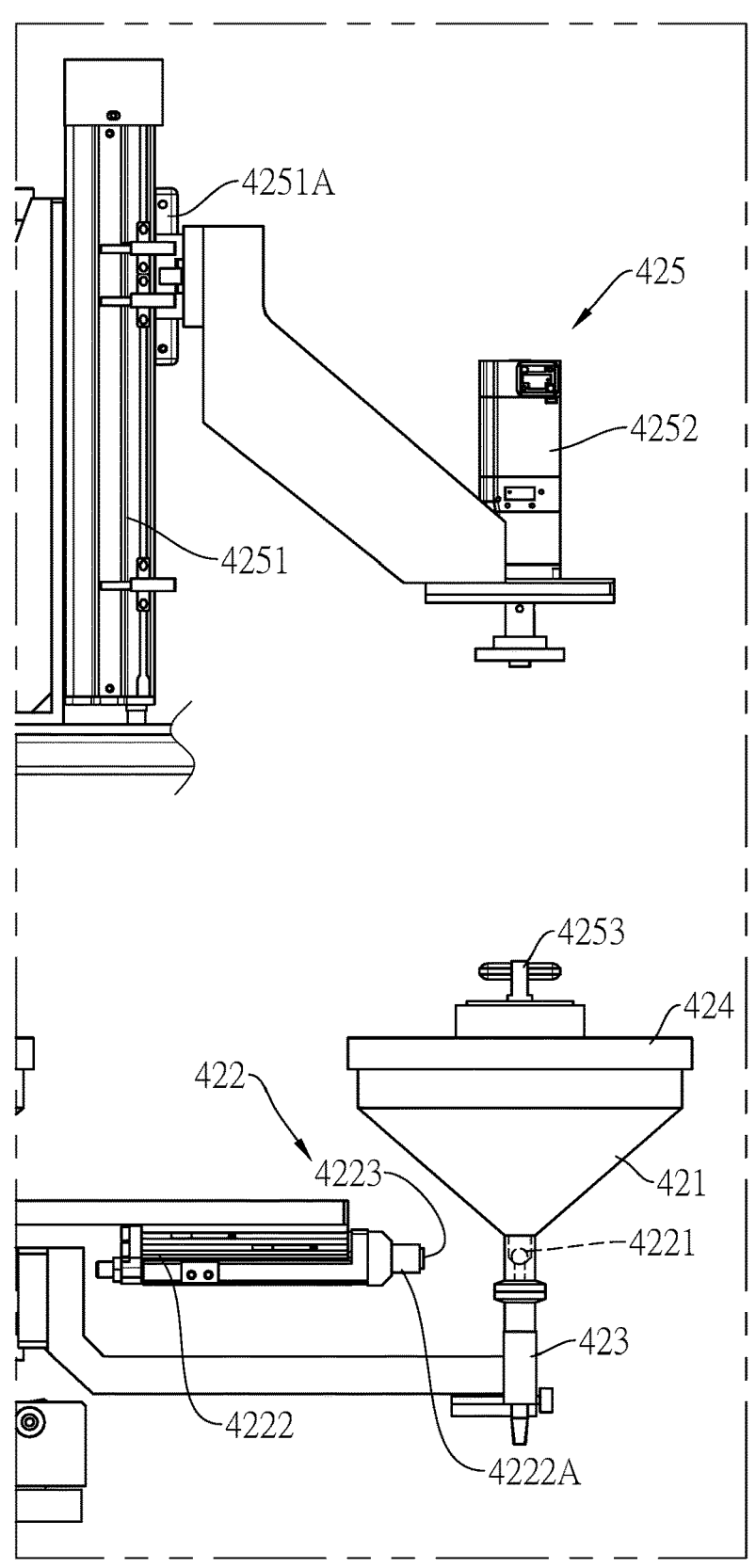
FIGS. 23 and 24 are enlarged side views of the container-handling device of the cell passaging device in FIG. 1, showing a stirring motor moved downward to connect a stirrer.

With reference to FIGS. 23 and 24, after the solutions with detached cells from all cell culture containers 91 are collected in the funnel 421, the funnel-positioning table 41 moves the gravitational liquid-splitting device 42 clockwise to the position above the two centrifuge containers 92, and meanwhile the slider 4251A of the stirring assembly 425 moves down to connect the stirring motor 4252 to the upper end of the stirrer 4253. The stirring motor 4252 drives the stirrer 4253 to keep stirring the solution with detached cells in the funnel 421.

With reference to FIGS. 25 and 28, then, the valve actuator 4222 of the dispensing valve 422 moves the second ferromagnetic part 4223 toward the first ferromagnetic part 4221 to the open position to move the first ferromagnetic part 4221 such that the solution with detached cells in the funnel 421 is split equally between the two centrifuge containers 92.

With reference to FIG. 4, finally, the two centrifuge containers 92 are moved to the container-handling device 20 by the primary container-moving device 50, and then moved into the centrifuge 70 by the auxiliary container-moving device 60 to perform centrifugation. After the centrifugation, the two centrifuge containers 92 are ready for subsequent cell passaging operations.

The cell passaging method in accordance with the present invention is not limited to aforementioned as long as contents in the cell culture containers 91 are split equally between the two centrifuge containers 92 by using the gravitational liquid-splitting device 42, and then the two centrifuge containers 92 are disposed oppositely in the centrifuge 70 to perform centrifugation to separate the cells from the solution.

In addition to performing the abovementioned cell passaging method, the cell passaging device is also configured to automatically perform various processes related to cell culture processing, such as primary specimen cells extraction process, cell culture container medium exchange process, cell culture container optical inspection process, and some of the cell cryopreservation processes such as cryovial dispensing, partial cell thawing process, and cell solution bottling for shipping process.

In summary, liquid (solution with detached cells) in the funnel 421 automatically flows downward into the centrifuge containers 92 due to gravity because the liquid-splitting part 423 of the gravitational liquid-splitting device 42 is disposed under the funnel 421, the input channel 4231 extends upward and downward, and meanwhile the output channels 4232 extend inclinedly downward; therefore, no liquid residue is left in the funnel 421, the input channel 4231, and the output channel 4232.

As a result, the present invention prevents loss of cells during transferring operation, avoids damage to the cells under pressurization by using pump, and effectively automates the process of collecting solution with detached cells together and then split the collected solution with detached cells equally between the two centrifuge containers, thereby improving efficiency of cell passaging and reducing cost of cell passaging.

Moreover, with the stirrer 4253 of the gravitational liquid-splitting device 42 continuously stirring the solution with detached cells in the funnel, 421, the present invention prevents cells from clustering together or adhering to surfaces of the funnel 421 or channels, thereby keeping flow rates in the two output channels 4232 remain equal and ensuring the solution with detached cells is split equally between the two centrifuge containers 92.

Finally, the cell passaging device replaces traditional manual shaking operation by automatically swaying the cell culture container 91, transferring the solution with detached cells into the gravitational liquid-splitting device 42, and splitting the solution with detached cells equally between the two centrifuge containers 92, thereby reducing labor-intensity for the cell passaging operation. As a result, the present invention has advantages such as high efficiency, stable quality, and reducing risk of contamination in cell passaging processes.

Even though numerous characteristics and advantages of the present invention have been set forth in the foregoing description, together with details of the structure and features of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. A gravitational liquid-splitting device comprising:
a funnel having an inner space and a bottom opening connected to the inner space;
a dispensing valve mounted to the funnel and configured to close or open the bottom opening of the funnel;
a liquid-splitting part connected to a bottom of the funnel and having:
an input channel formed in the liquid-splitting part and extending upward and downward; an upper end of the input channel forming an input opening on a top of the liquid-splitting part and connected to the bottom opening of the funnel; and
two output channels formed in the liquid-splitting part; each of the output channels having a first end and a second end; the first end connected to a lower end of the input channel; the second end extending inclinedly downward and connected to an exterior of the liquid-splitting part; and
a stirring assembly having
a funnel cover detachably covering an upper opening of the funnel; and
a stirrer connected to the funnel cover and configured to stir liquid in the funnel.

2. The gravitational liquid-splitting device as claimed in claim 1, wherein the liquid-splitting part has at least one auxiliary channel formed in the liquid-splitting part and having:
a third end connected to one of the two output channels; and
a fourth end extending inclinedly upward and connected to the exterior of the liquid-splitting part.

3. The gravitational liquid-splitting device as claimed in claim 2, wherein the at least one auxiliary channel includes two auxiliary channels; each of the two auxiliary channels is connected to a respective one of the two output channels and extends along a same straight line with said output channel.

4. The gravitational liquid-splitting device as claimed in claim 1, wherein the dispensing valve has:
a first ferromagnetic part movably disposed in the inner space of the funnel and driven by a weight of the first ferromagnetic part to move toward the bottom opening of the funnel to close the bottom opening;
a valve actuator disposed outside of the funnel; a moving end of the valve actuator being movable toward the first ferromagnetic part to an open position;
a second ferromagnetic part mounted to the moving end of the valve actuator; the second ferromagnetic part and the first ferromagnetic part magnetically attracting or repelling each other;
wherein, when the moving end of the valve actuator is at the open position, the first ferromagnetic part is driven by the second ferromagnetic part to open the bottom opening of the funnel.

5. The gravitational liquid-splitting device as claimed in claim 3, wherein the dispensing valve has:
a first ferromagnetic part movably disposed in the inner space of the funnel and driven by a weight of the first ferromagnetic part to move toward the bottom opening of the funnel to close the bottom opening;
a valve actuator disposed outside of the funnel;
a moving end of the valve actuator being movable toward the first ferromagnetic part to an open position;
a second ferromagnetic part mounted to the moving end of the valve actuator; the second ferromagnetic part and the first ferromagnetic part magnetically attracting or repelling each other;
wherein, when the moving end of the valve actuator is at the open position, the first ferromagnetic part is driven by the second ferromagnetic part to open the bottom opening of the funnel.

6. A cell passaging device, configured to concentrate contents collected from multiple cell culture containers into two centrifuge containers; the cell passaging device comprising:
a base;
a container-handling device mounted on the base and having:
a container-positioning table rotatably or movably mounted on the base;
multiple container holders pivotally mounted on the container-positioning table; each of the container holders configured to accommodate one of the cell culture containers or one of the centrifuge containers, and being pivotable to an emptying angle to empty contents in the cell culture container or the centrifuge container; and
multiple container-driving assemblies; each of the container-driving assemblies controlling an angle of a respective one of the container holders and configured to rotate the respective one of the container holders to the emptying angle or to sway the respective one of the container holders;
wherein, the container-positioning table is configured to move each of the container holders to a first injection position; and
a liquid equal-splitting device disposed on a side of the container-handling device; the liquid equal-splitting device having:
a funnel-positioning table rotatably or movably mounted on the base; and
at least one said gravitational liquid-splitting device as claimed in claim 1 mounted on the funnel-positioning table;
wherein, the funnel-positioning table is configured to move the at least one gravitational liquid-splitting device from a position under the first injection position to a position above the two centrifuge containers such that the liquid in the funnel of the at least one gravitational liquid-splitting device flows into the two centrifuge containers via the two output channels respectively.

7. The cell passaging device as claimed in claim 6, wherein:
the container-positioning table is configured to move each of the container holders to a second injection position; and
the cell passaging device has a liquid solution injection device; the liquid solution injection device is mounted on the base and has multiple injection heads; each of the injection heads is connected to a container with a kind of liquid solution and is movable to a position above the second injection position to inject the liquid solution in the container into the cell culture container located in the container holder in the second injection position.

8. The cell passaging device as claimed in claim 6, wherein:

the container-positioning table of the container-handling device is configured to move each of the container holders to a container-receiving position or a container output position;

the cell passaging device has:

a primary container-moving device configured to move each of the two centrifuge containers from the position under the at least one gravitational liquid-splitting device to the container holder at the container-receiving position;

a centrifuge disposed on a side of the container-handling device; and an auxiliary container-moving device configured to move the centrifuge container in the container holder at the container output position into the centrifuge, and configured to move the centrifuge container in the centrifuge back into the container holder at the container output position.

9. The cell passaging device as claimed in claim 6, wherein:

the container-positioning table of the container-handling device is configured to move each of the container holders to a container-receiving position or a container output position;

the cell passaging device has:

an optical inspection device disposed on a side of the container-handling device and configured to calculate the number of detached cells in the cell culture containers; and an auxiliary container-moving device configured to move the cell culture container in the container holder at the container output position into the optical inspection device, and configured to move the cell culture container in the optical inspection device back into the container holder at the container output position.

10. The cell passaging device as claimed in claim 8, wherein:

the container-positioning table of the container-handling device is rotatably mounted on the base and configured to move each of the container holders to circulate between the container-receiving position, the container output position, the first injection position, and a second injection position;

the cell passaging device has:

a liquid solution injection device mounted on the base and having multiple injection heads; each of the injection heads connected to a container with a kind of liquid solution and being movable to a position above the second injection position to inject the liquid solution in the container into the cell culture container located in the container holder at the second injection position; and an optical inspection device disposed on a side of the container-handling device and configured to calculate the number of detached cells in the cell culture containers; and the auxiliary container-moving device is configured to move the cell culture container in the container holder at the container output position into the optical inspection device, and configured to move the cell culture container in the optical inspection device back into the container holder at the container output position;

wherein, the second injection position and the container output position are oppositely disposed on the container-handling device; the centrifuge, the auxiliary container-moving device, and the optical inspection device are disposed on a side, which is toward the container output position, of the container-handling device; the liquid solution injection device is disposed on a side, which is toward the second injection position, of the container-handling device.

11. The cell passaging device as claimed in claim 6, wherein:

the container-positioning table of the container-handling device is configured to move each of the container holders to a container-receiving position or a container output position; and the cell passaging device has a primary container-moving device; the primary container-moving device is configured to move the cell culture container in the container holder at the container-receiving position to the position under the at least one gravitational liquid-splitting device such that the liquid in the funnel of the at least one gravitational liquid-splitting device flows into the cell culture container.

12. A cell passaging method for concentrating contents collected from multiple cell culture containers into two centrifuge containers; the cell passaging method comprising steps of: using the gravitational liquid-splitting device as claimed in claim 1 to split contents in the cell culture containers equally between the two centrifuge containers, then disposing the two centrifuge containers oppositely in a centrifuge and using the centrifuge to perform centrifugation.

* * * * *